(12) United States Patent
Kohrs et al.

(10) Patent No.: US 6,740,091 B2
(45) Date of Patent: *May 25, 2004

(54) LORDOTIC SPINAL IMPLANT

(75) Inventors: Douglas W. Kohrs, Edina, MN (US); Paul M. Sand, Roseville, MN (US)

(73) Assignee: Sulzer Spine-Tech Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/273,706

(22) Filed: Oct. 16, 2002

(65) Prior Publication Data

US 2003/0045938 A1 Mar. 6, 2003

Related U.S. Application Data

(63) Continuation of application No. 09/686,922, filed on Oct. 11, 2000, now abandoned, which is a continuation of application No. 09/036,165, filed on Mar. 6, 1998, now Pat. No. 6,165,219, which is a continuation-in-part of application No. 08/812,791, filed on Mar. 6, 1997, now abandoned.

(51) Int. Cl.[7] ................................. A61F 2/44

(52) U.S. Cl. ........................... 606/79; 606/90

(58) Field of Search ................. 623/17.11; 606/61, 606/62, 79

(56) References Cited

U.S. PATENT DOCUMENTS

| | | |
|---|---|---|
| 57,124 A | 8/1866 | Gregg |
| 2,388,022 A | 10/1945 | Tucker et al. |
| 3,850,158 A | 11/1974 | Elias et al. |
| 4,743,256 A | 5/1988 | Brantigan |
| 4,834,757 A | 5/1989 | Brantigan |
| 4,878,915 A | 11/1989 | Brantigan |
| 4,961,740 A | 10/1990 | Ray et al. |
| 5,015,247 A | 5/1991 | Michelson |
| 5,098,435 A | 3/1992 | Stednitz et al. |
| 5,147,402 A | 9/1992 | Bohler et al. |
| 5,425,772 A * | 6/1995 | Brantigan ............. 623/17.11 |
| 5,443,514 A | 8/1995 | Steffee |
| 5,458,638 A | 10/1995 | Kuslich et al. |
| 5,484,437 A * | 1/1996 | Michelson ............. 606/61 |
| 5,489,307 A * | 2/1996 | Kuslich et al. ......... 128/898 |
| 5,489,308 A | 2/1996 | Kuslich et al. |
| 5,505,732 A | 4/1996 | Michelson |
| 5,534,031 A | 7/1996 | Matsuzaki et al. |

(List continued on next page.)

FOREIGN PATENT DOCUMENTS

| | | | |
|---|---|---|---|
| EP | 0 646 366 A1 | 4/1995 | |
| EP | 0 734 703 A2 | 10/1996 | |
| WO | WO 91/06261 * | 5/1991 | ............. 623/17.11 |
| WO | WO 95/22946 | 8/1995 | |
| WO | WO 95/31947 | 11/1995 | |
| WO | WO 96/27345 | 9/1996 | |

OTHER PUBLICATIONS

Publication entitled *Ray Cervical Threaded* Fusion Cage of Surgical Dynamics, Concord, California, dated 1994.

Publication entitled *Varlock* of Biomat, dated Nov. 1994.

Mark Bernhardt, "Normal Spinal Anatomy: Normal Sagittal Plan Alignment," *The Textbook of Spinal Surgery, Second Edition*, Chapter 16 (pp. 1840191), Birdwell editors, Lippincott–Raven Publishers, 1997.

*Primary Examiner*—David H. Willse
*Assistant Examiner*—Suzette J. Jackson
(74) *Attorney, Agent, or Firm*—Merchant & Gould P.C.

(57) ABSTRACT

A lordotic implant has a frusto-conical shape with external threads. Prior to placement of the implant, vertebrae are distracted in a manner to provide a desired lordosis between the vertebrae. The pre-distracted vertebrae are then tapped to provide a tapped bore having a geometry matching the conical geometry of the implant. The threaded implant is then placed within the pre-tapped conical bore.

38 Claims, 21 Drawing Sheets

U.S. PATENT DOCUMENTS

| | | |
|---|---|---|
| 5,562,371 A | 10/1996 | Reed |
| 5,593,409 A | 1/1997 | Michelson |
| 5,609,635 A | 3/1997 | Michelson |
| 5,653,761 A | 8/1997 | Pisharodi |
| 5,669,909 A * | 9/1997 | Zdeblick et al. .............. 606/61 |
| 5,741,253 A | 4/1998 | Michelson |
| 5,749,916 A | 5/1998 | Richelsoph |
| 5,766,252 A | 6/1998 | Henry et al. |
| 5,769,897 A | 6/1998 | Härle |
| 5,782,919 A | 7/1998 | Zdeblick et al. |
| 5,797,909 A | 8/1998 | Michelson |
| 5,865,847 A | 2/1999 | Kohrs et al. |
| 5,897,593 A | 4/1999 | Kohrs et al. |
| 5,906,616 A | 5/1999 | Pavlov et al. |
| 5,984,922 A | 11/1999 | McKay |
| 5,984,967 A | 11/1999 | Zdeblick et al. |
| 6,059,790 A * | 5/2000 | Sand et al. .................... 606/99 |
| 6,120,506 A | 9/2000 | Kohrs et al. |
| 6,165,219 A * | 12/2000 | Kohrs et al. ............. 623/17.11 |
| 6,174,311 B1 * | 1/2001 | Branch et al. ................ 606/61 |
| 6,210,412 B1 | 4/2001 | Michelson |
| 2001/0031254 A1 | 10/2001 | Bianchi et al. |
| 2002/0106393 A1 | 8/2002 | Bianchi et al. |

* cited by examiner

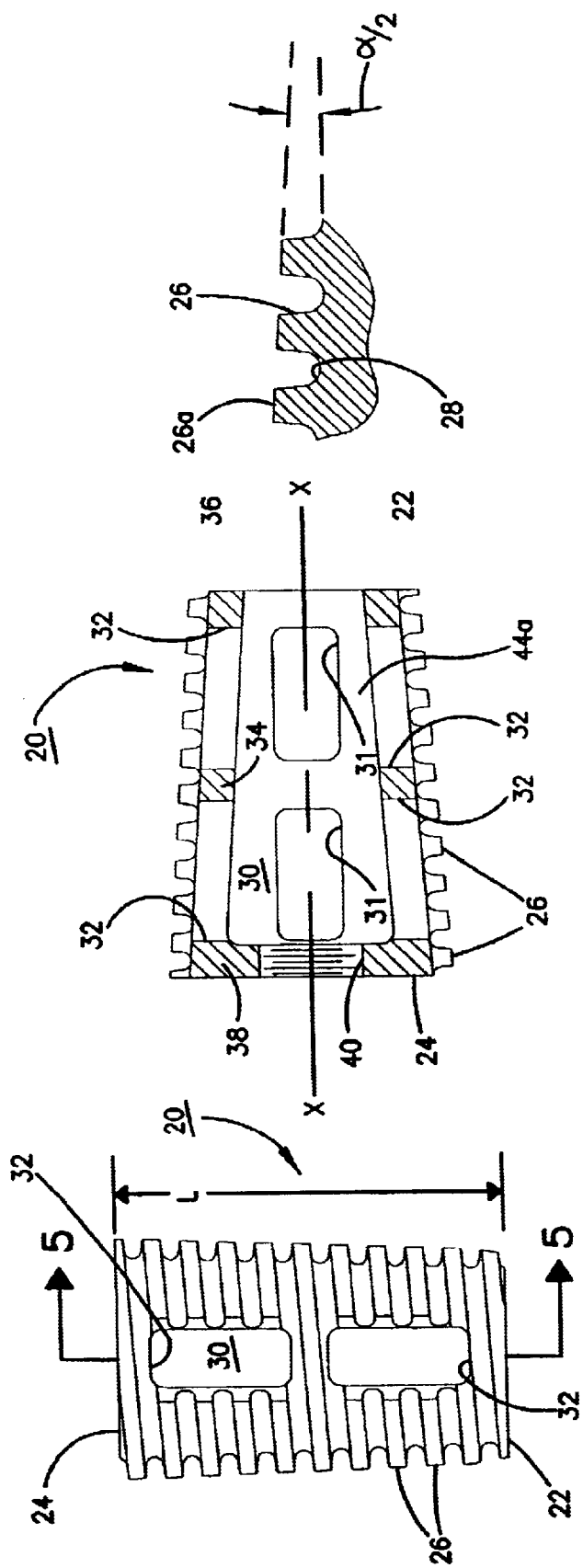

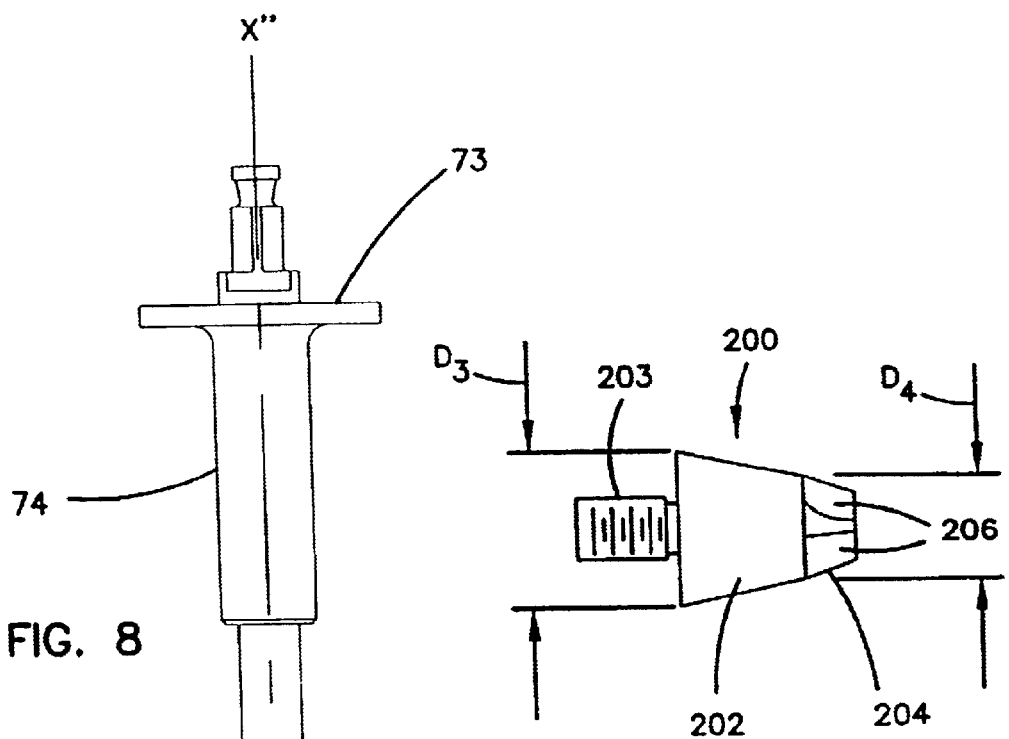
FIG. 8
FIG. 10
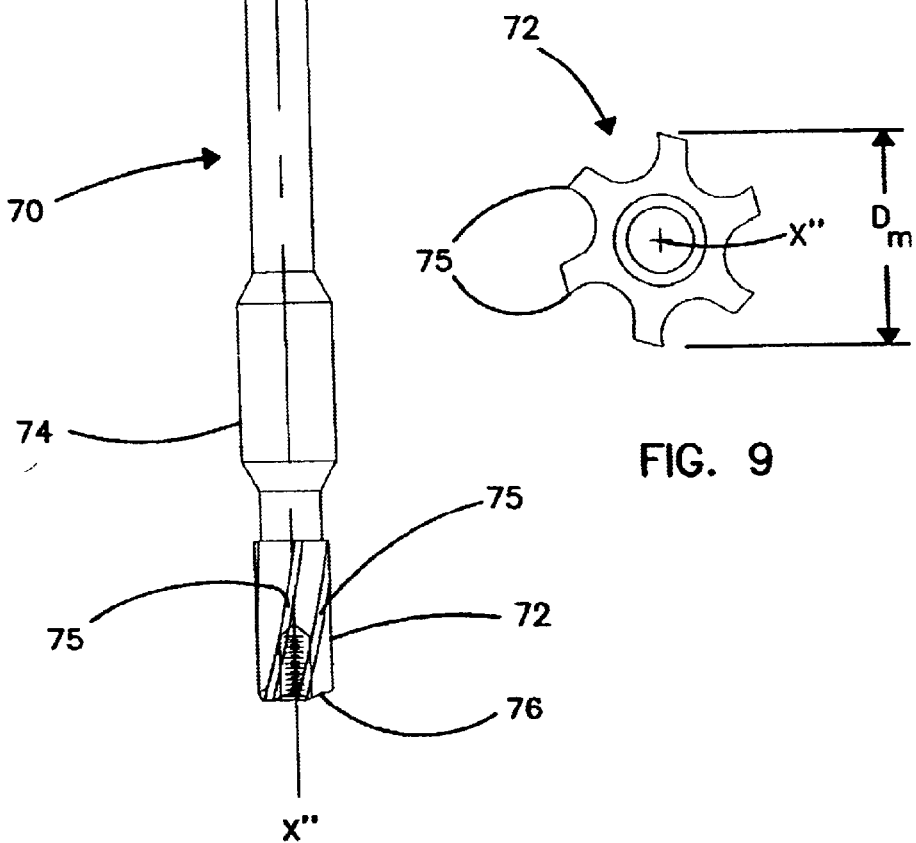
FIG. 9

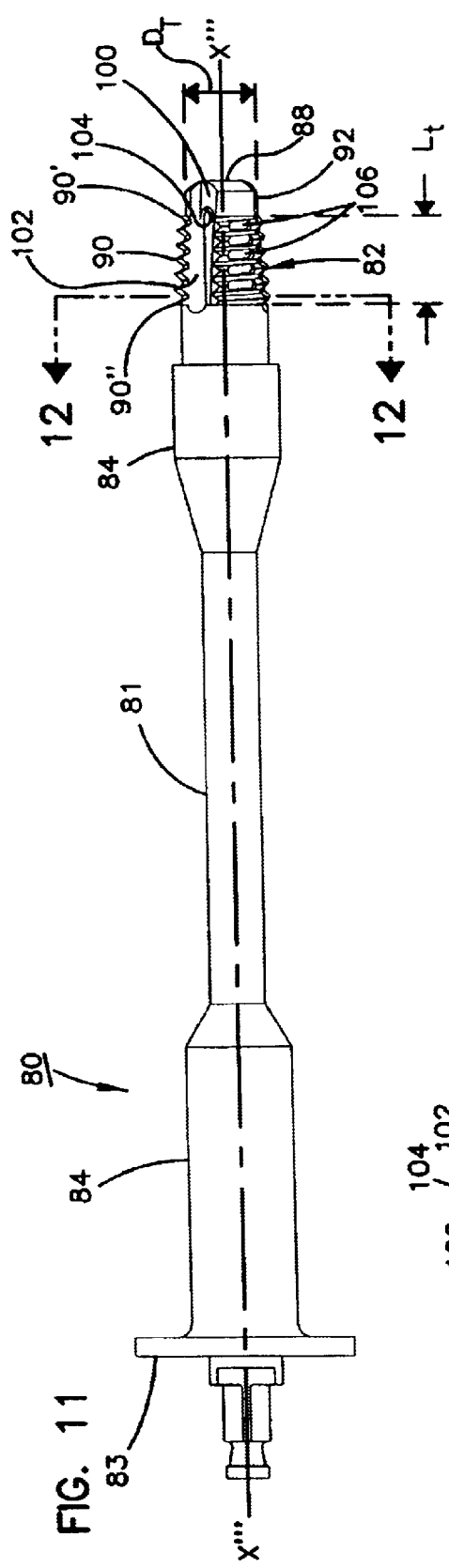
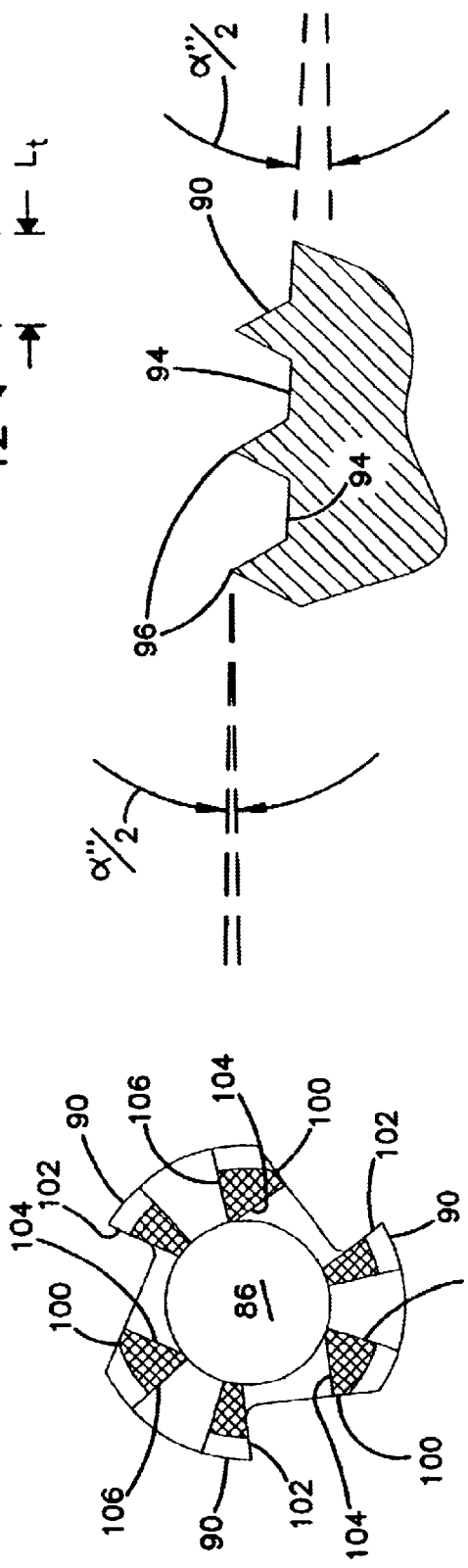
FIG. 11
FIG. 12
FIG. 13

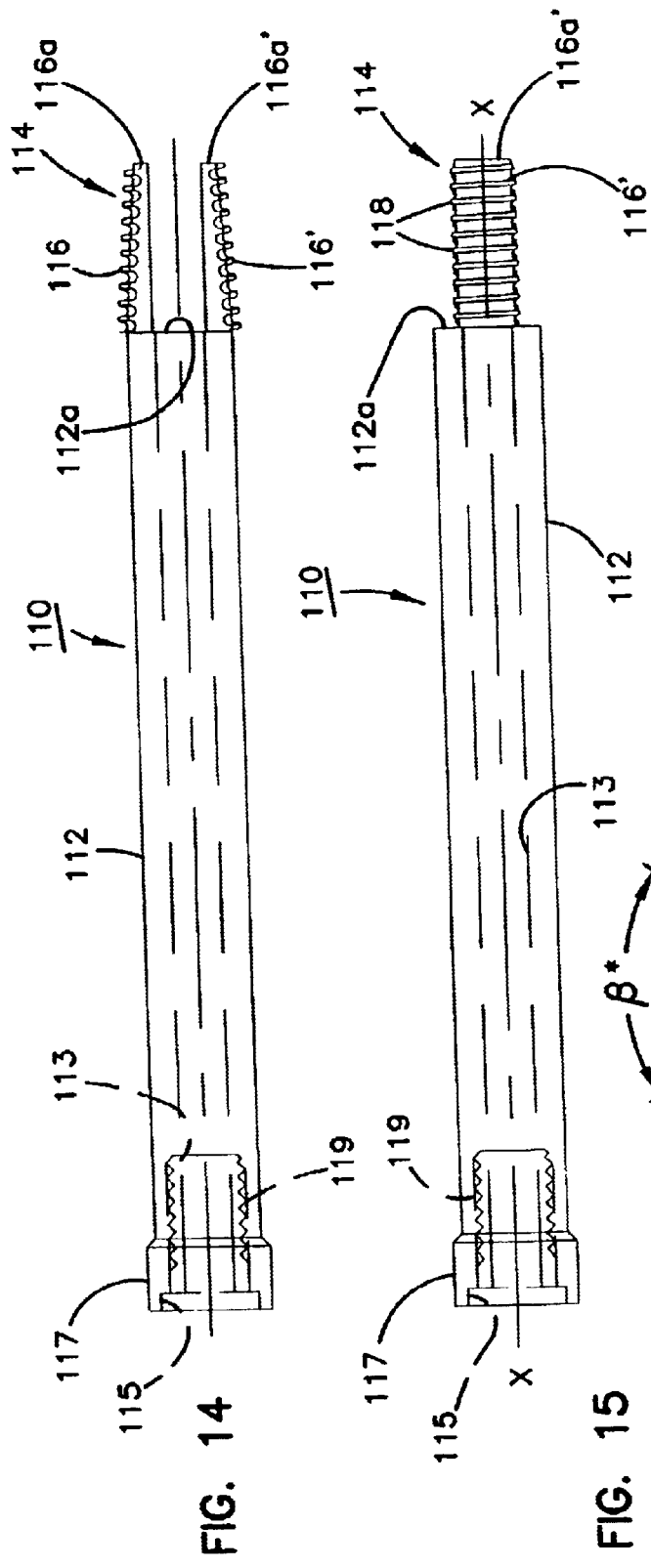
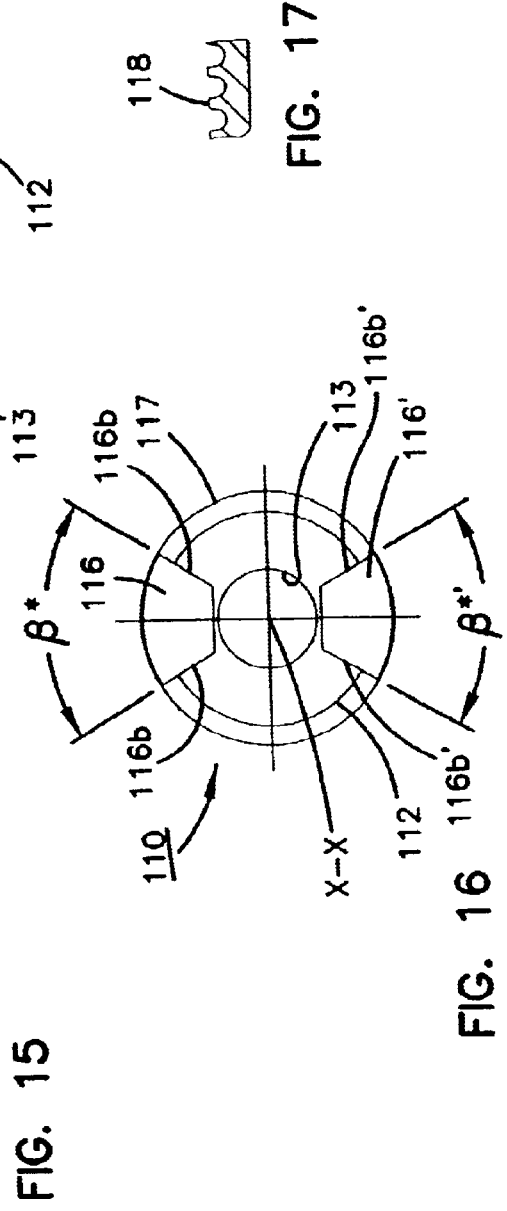

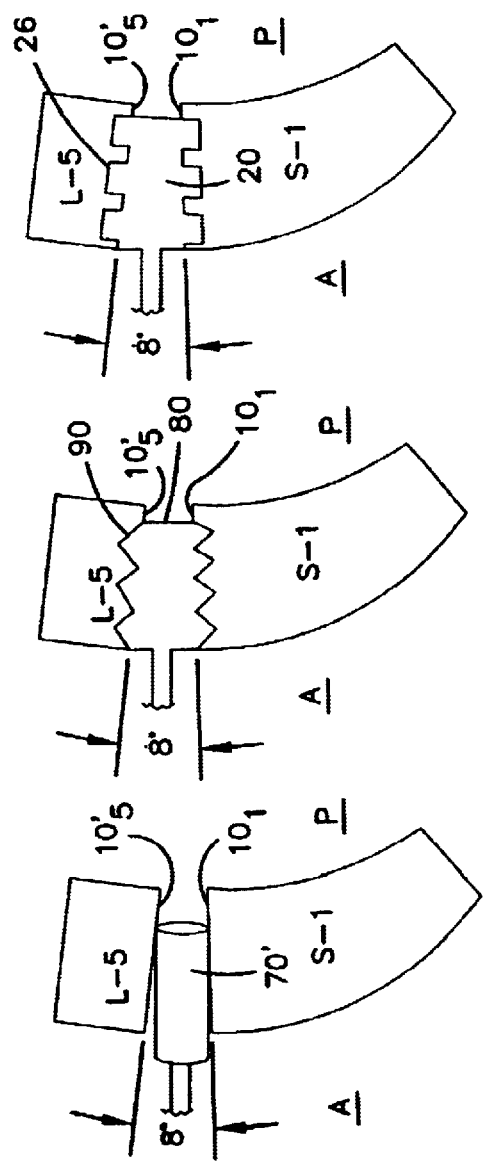

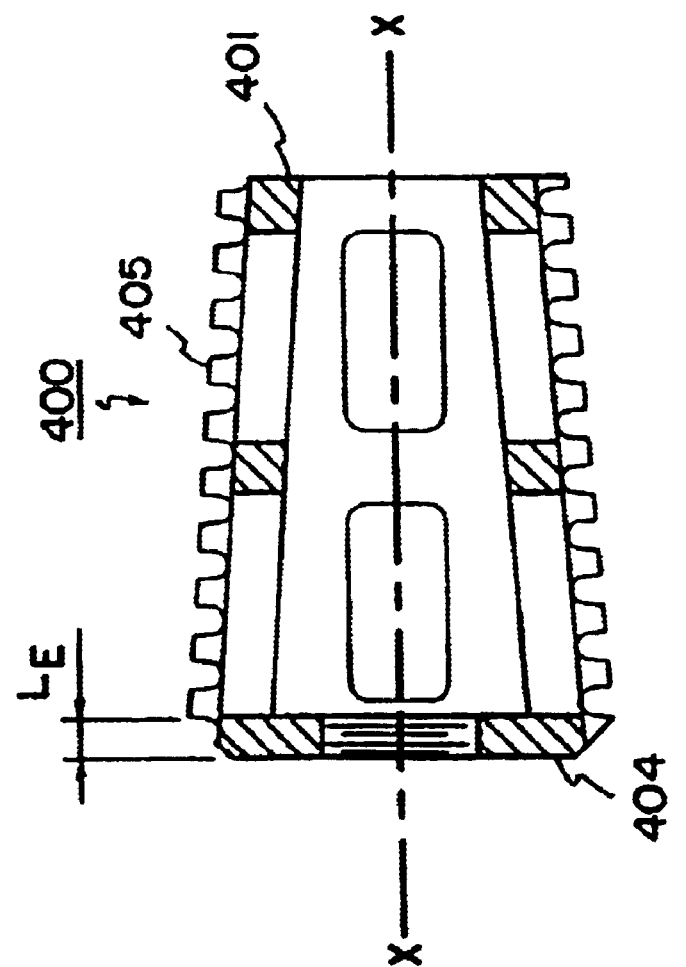
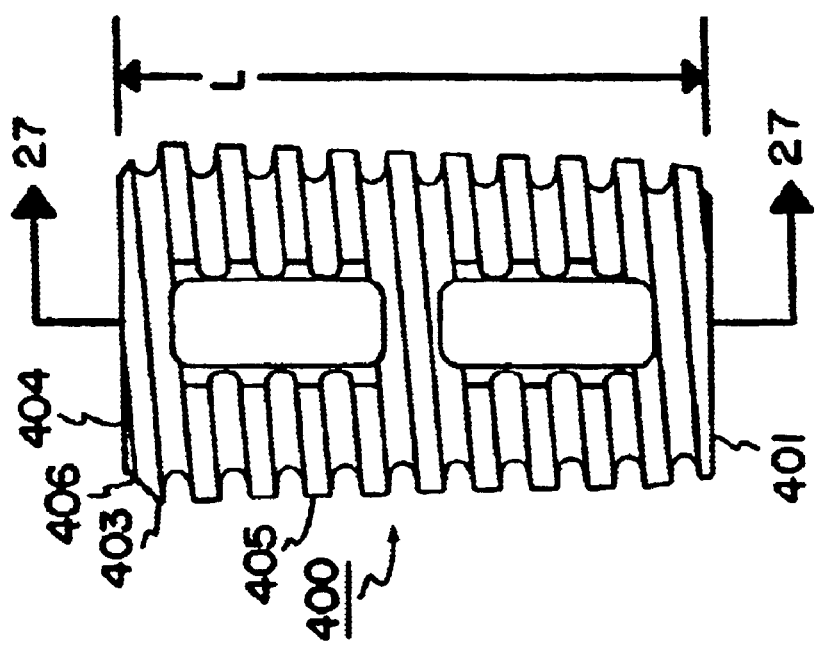
FIG. 27
FIG. 26

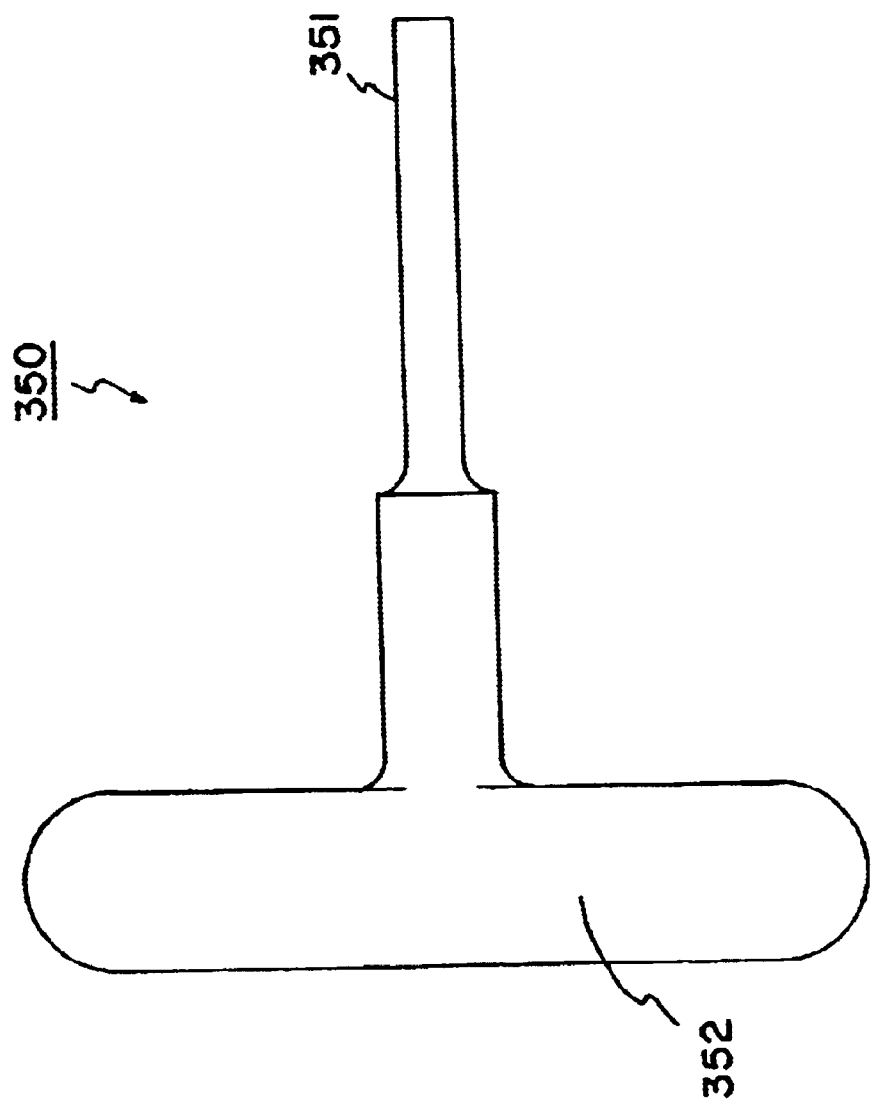

LORDOTIC SPINAL IMPLANT

CROSS-REFERENCE TO RELATED APPLICATIONS

The present application is a continuation application of U.S. Ser. No. 09/686,922, filed Oct. 11, 2000 now abandoned, which is a continuation application of U.S. Ser. No. 09/036,165, filed Mar. 6, 1998, issued as U.S. Pat. No. 6,165,219, which is a continuation-in-part application of U.S. Ser. No. 08/812,791, filed Mar. 6, 1997 abandoned, the entire disclosures of which are incorporated herein by reference.

I. BACKGROUND OF THE INVENTION

1. Field of the Invention

This invention pertains to spinal implants and surgical procedures for use in spinal stabilization. More particularly, this invention pertains to an apparatus and method for implanting a tapered implant between two vertebrae.

2. Description of the Prior Art

Chronic back problems can cause pain and disability for a large segment of the population. In many cases, the chronic back problems are attributed to relative movement between vertebrae in the spine.

Orthopedic surgery includes procedures to stabilize vertebrae. Common stabilization techniques include fusing the vertebrae together. Fusion techniques include removing disk material which separates the vertebrae and impacting bone into the disk area. The impacted bone fuses with the bone material in the vertebrae to thereby fuse the two vertebrae together.

To increase the probability of a successful fusion, spinal implants have been developed. Commonly assigned U.S. Pat. No. 5,489,307 discloses a hollow threaded cylindrical implant. That patent also discloses a method of placing the implant between two vertebrae.

The method of U.S. Pat. No. 5,489,307 discloses parallel distraction of opposing vertebrae prior to placing an implant. However, not all vertebrae are in parallel opposition. A normal and healthy spine has a natural curvature referred to as lordosis. As a result of the curvature, opposing vertebrae are positioned with their end plates in non-parallel alignment depending upon the position in the spine. For example, in the lumbar region of the spine, the end plates of the L-4 and L-5 vertebrae may be at an angle of about 3°–15°. Similarly, the opposing end plates of the L-5 and S-1 vertebrae may be at about 8°–16° lordosis. The actual amount of lordosis varies with the location of the spine and varies from patient to patient. It is desirable to provide an implant which maintains or achieves a desired lordosis between opposing vertebrae and a method of placing the implant.

II. SUMMARY OF THE INVENTION

According to one embodiment of the present innovation, a spinal implant is disclosed having a taper from a leading end to a trailing end equal to a desired lordosis.

In an alternative embodiment, a spinal implant can have two tapers. According to this embodiment the implant has a first taper diverging away from the axis of the implant from the leading end to a terminal end. A second taper diverges away from the axis of the implant from the terminal end to the leading end. The tapers meet at the "trailing end rise". The "trailing end rise" (TRE) and the terminal end are collectively referred to as the trailing end. In a preferred embodiment the implant has a terminal end and a leading end which are of substantially equal diameters.

The method of the invention includes placing a tapered distraction plug into the disk space between the vertebrae on one side of the vertebrae. On the opposite side of the vertebrae, a tapered tap is used to tap a thread pattern into the opposing vertebrae. The implant is placed into the tapped space.

III. BRIEF DESCRIPTION OF THE DRAWINGS

FIG. 4 is a top plan view of the implant of FIG. 1 taken 90° from the view of FIG. 1 (the opposite side being identical in appearance);

FIG. 5 is a view taken along line 5—5 of FIG. 4;

FIG. 6 is an enlarged cross-sectional view of thread detail of the implant of FIG. 1;

FIG. 8 is a side elevation view of a pre-boring tool for use in the surgical method of the present invention;

FIG. 9 is an elevation view of a distal end of the tool of FIG. 8;

FIG. 10 is a side elevation view of guide pin for use with the pre-boring tool of FIG. 8;

FIG. 11 is a side elevation view of a tap according to the present invention;

FIG. 12 is a view taken along line 12—12 of FIG. 11;

FIG. 13 is a cross-sectional view of threads of the tap of FIG. 11;

FIG. 14 is a side elevation view of a driver for use in the method of the present invention;

FIG. 15 is a top plan view of the driver of FIG. 14;

FIG. 16 is an elevation view of a distal end of the driver of FIG. 14;

FIG. 17 is an enlarged cross-sectional view of a thread pattern on the driver of FIG. 14;

FIG. 21 is the view of FIG. 20 showing boring with the tool of FIG. 10;

FIG. 22 is the view of FIG. 21 showing tapping with the tool of FIG. 11;

FIG. 23 is the view of FIG. 22 showing placement of the implant of FIG. 1;

FIG. 24 is an anterior to posterior view of FIG. 23;

FIG. 26 is a top plan view of the implant of FIG. 25 taken 90° from the view of FIG. 25 (the opposite side being identical in appearance);

FIG. 27 is a view taken along line 27—27 of FIG. 26;

FIG. 37 is a top view of a T-device for removal of a distraction plug from a tool.

IV. DESCRIPTION OF THE PREFERRED EMBODIMENT

With reference now to the various drawing Figures in which identical elements are numbered identically throughout, a description of the preferred embodiment under the present invention will now be provided. As will become apparent, the present invention utilizes certain surgical methods and tools disclosed more fully in U.S. Pat. No. 5,489,307 incorporated herein by reference.

Figure 18:
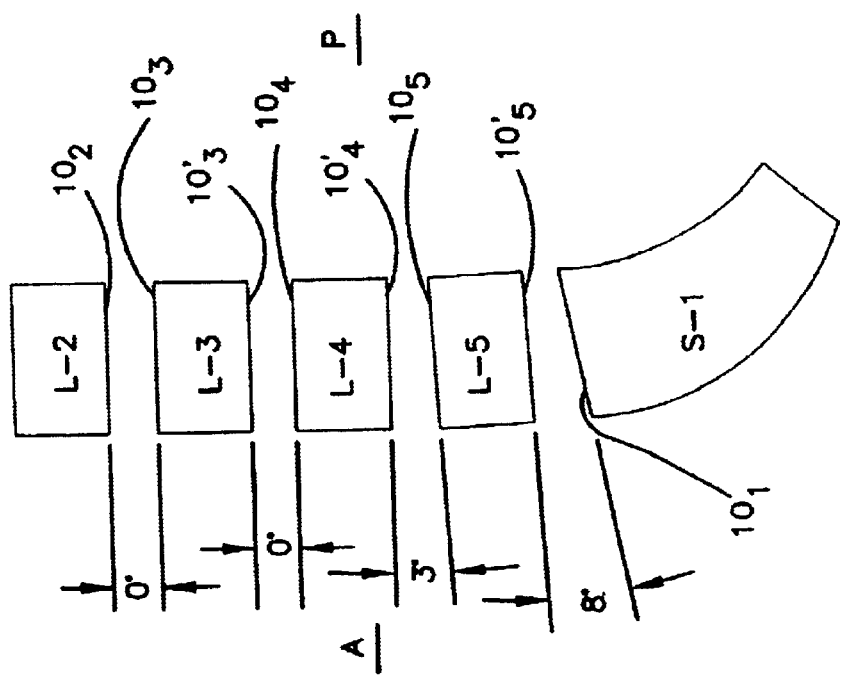
FIG. 18 is a schematic side elevation view of vertebrae in the spine.

With initial reference to FIG. 18, a healthy spine is schematically shown to illustrate lordosis in the spine. As shown in the example of FIG. 18, the end plates $10_2$, $10_3$ of vertebrae L-2 and L-3 are in parallel alignment. Similarly, the end plates $10_3'$ and $10_4$ of vertebrae L-3 and L-4 are in parallel alignment. However, the end plates $10_4'$ and $10_5$ of vertebrae L-4 and L-5 are at a 3° angle with the widest separation on the anterior, A, side of the spine and the narrowest separation on the posterior, P, side of the spine. Similarly, the end plates $10_5'$ and $10_1$ of vertebrae L-5 and S-1 are at an 8° angle (with the widest separation on the anterior side of the spine). It will be appreciated that the examples given are illustrative only. The actual degree of lordosis will vary from patient to patient and within the region of the spine.

Where a physician determines that spinal fusion is desired between lordotically separated vertebrae, the present invention is directed to an apparatus and method for fusing the opposing vertebrae while maintaining lordosis. Further, where an attending physician determines that fusion is desirable and further determines that increased lordosis is desirable, the present invention is directed towards an apparatus and method for both fusing the spine and for increasing the amount of lordosis between the vertebrae to a degree of separation determined by the attending physician. The present invention will be described in application to the latter example illustrated in FIG. 19 where the end plates $10_5'$ and $10_1$ of opposing vertebrae L-5 and S-1 are parallel and a physician determines that an 8° lordosis is desirable in addition to placing a fusion implant between the vertebrae.

A. Implant.

With initial reference to FIGS. 1–6, an implant 20 according to the present invention is shown. The implant 20 has a longitudinal axis X—X extending from a leading end 22 to a trailing end 24.

The implant 20 has a substantially frusto-conical shape with a conical angle α equal to a desired lordosis between the vertebrae into which the implant 20 is to be placed. In the example given, angle α is 8°. However, it will be appreciated that such implants 20 will be available in a wide variety of sizes. For example, such implants may be provided having angles α ranging from 1° to 20° in 1° increments to permit an attending physician to select a desired implant to attain a desired lordosis. Further, such implants can be provided in varying sizes (i.e., the diameters of the implants) to accommodate desired distraction and lordosis between opposing vertebrae.

The implant 20 has helical threads 26 surrounding the conical surface of the implant 20. Shown best in FIG. 6, the threads 26 are generally square in cross-section with their flat outer peripheral surfaces 26a set at an angle of one-half α with respect to the longitudinal axis X—X and define valleys 28 between the threads 26.

At the leading end 22, the implant has a major diameter $D_M$ measured between diametrically opposite outer radial surfaces 26a of the threads 26 at the leading end 22. At the leading end 22, the implant 20 has a minor diameter $D_m$ measured as the distance across the implant 20 between the valleys 28 of the thread pattern 26.

At the trailing end 24, the implant 20 has a major diameter $D'_M$ measured between diametrically opposite outer radial surfaces 26a of threads 26 at the trailing end 24. Finally, at the trailing end 24, the implant 20 has a minor diameter $D'_m$ measured between diametrically opposite valleys 28 at the trailing end 24.

For purposes of illustration, representative sizings of the implant 20 will have a leading end major diameter $D_M$ of about 0.56 inches and a minor diameter $D_m$ at the leading end 22 of about 0.46 inches. At the trailing end 24, the major diameter $D'_M$ is about 0.69 inches and the minor diameter $D'_m$ is about 0.59 inches. The length L (FIG. 4) of the implant (measured from the leading end 22 to the trailing end 24) is about 0.95 inches. Again, it will be appreciated that the foregoing dimensions are illustrative only and the sizing can vary to accommodate a surgeon's selection of a desired sizing for placement into a disk space.

The implant 20 is hollow to present a hollow implant interior 30. FIG. 4 illustrates a top side of the implant 20. As shown, the implant includes axially aligned holes 32 extending through the conical wall of the implant into communication with the interior 30. The holes 32 are provided on diametrically opposite sides of the implant (i.e., the side of the implant opposite that shown in FIG. 4 is identical to that shown in FIG. 4). The holes 32 therefore extend completely through the implant 20 to define a hollow column through which bone may grow from opposing vertebrae after the implant is placed between the vertebrae and with the holes 32 facing the vertebrae.

The holes 32 on a given side (such as that shown in FIG. 4) are separated by a central reinforcing rib 34. Further, a reinforcing rib 36 is provided at the leading end 22 and a reinforcing rib 38 is provided at the trailing end 24 to resist compression forces on the implant 20 after it is placed between opposing vertebrae.

The trailing end 24 is provided with an axially positioned threaded bore 40, the purposes of which will be described. The leading end 22 is provided with an oval bore 42 having its major axis aligned with the opposing holes 32. Bone chips or other bone growth inducing substances may be placed into the interior of the implant 20 to promote fusion following placement of the implant 20 between opposing vertebrae.

Figure 1:
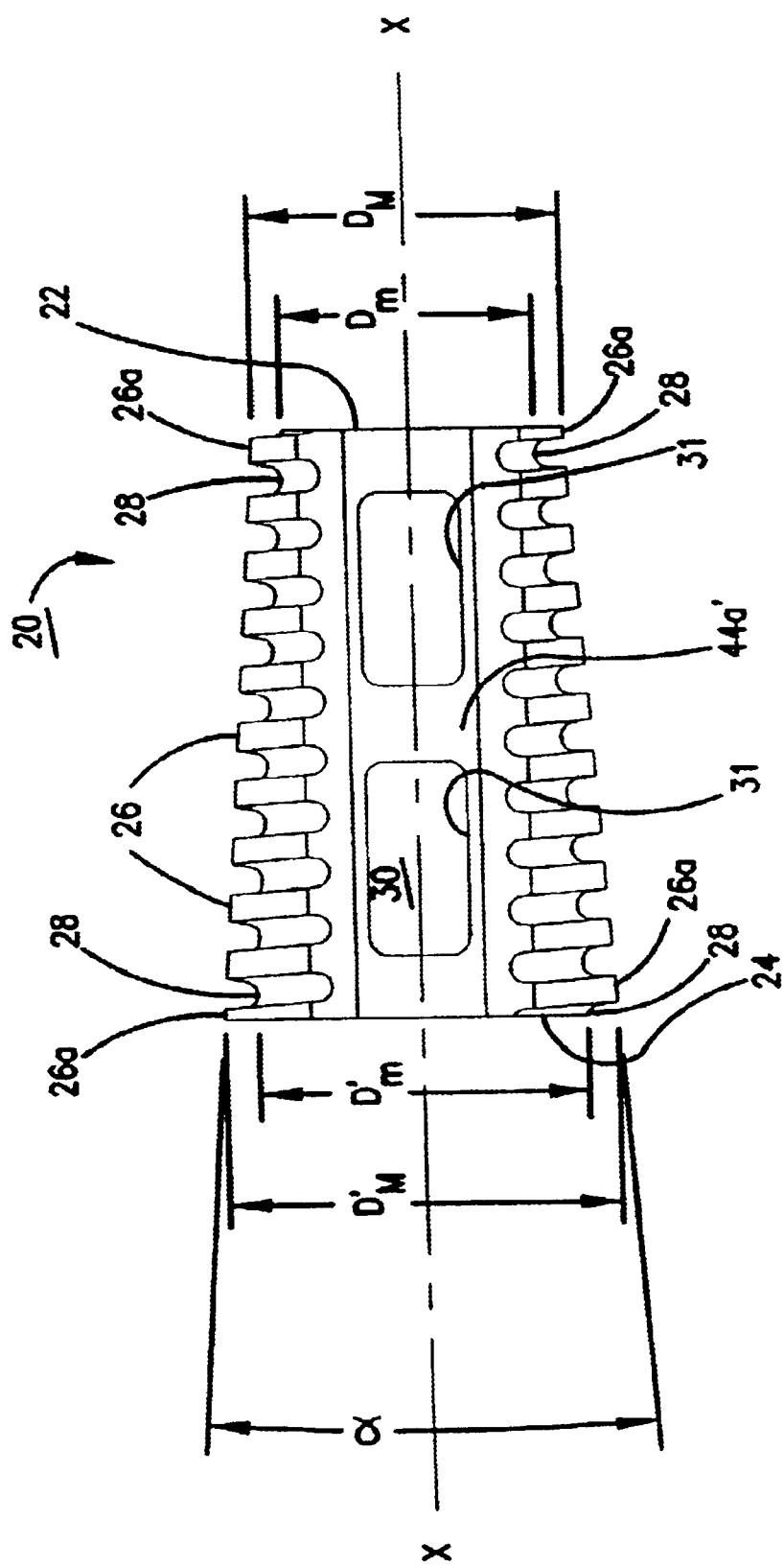
FIG. 1 is a right side elevation view of a lordotic implant according to the present invention (the opposite side being identical in appearance)
Figure 3:
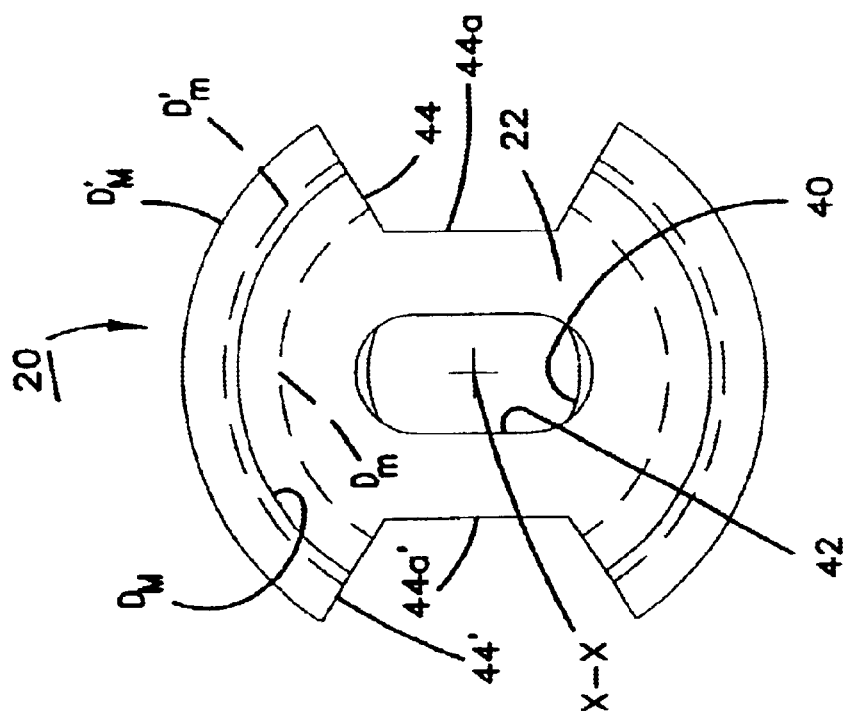
FIG. 3 is an end elevation of a leading end of the implant of FIG. 1.
Figure 2:
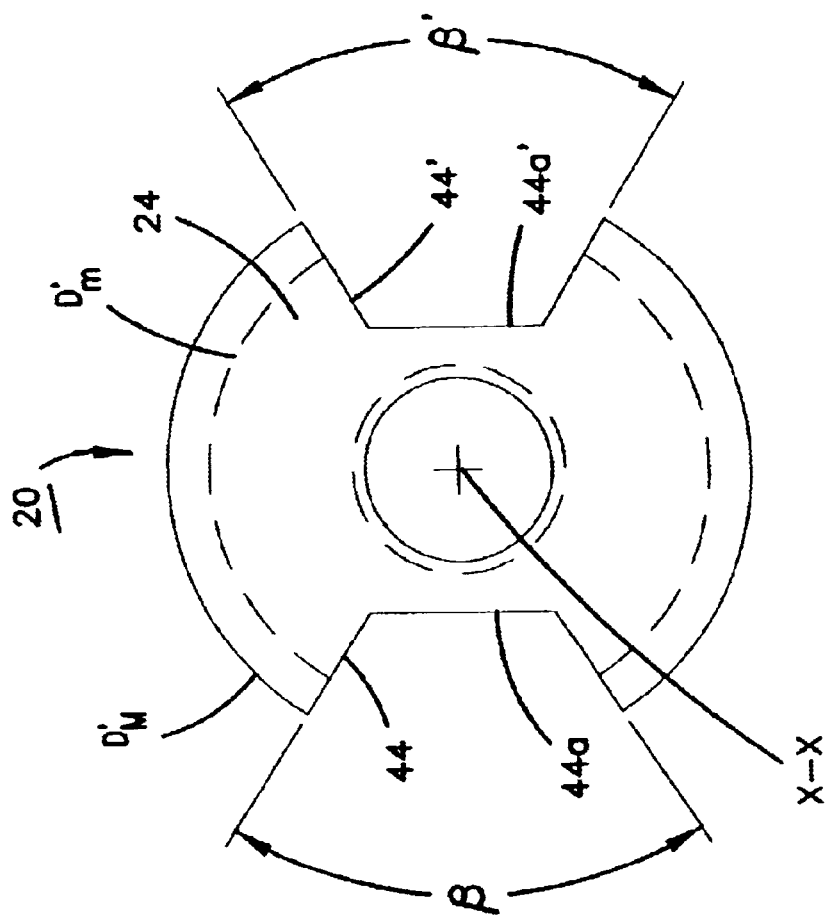
FIG. 2 is an elevation view of a trailing end of the implant of FIG. 1.

As best illustrated in FIGS. 1–3, the thread pattern 26 is not continuous. Instead, the sidewalls of the implant 20 are provided with cutouts 44,44' on the sides of the implant which are 90° offset from the sides containing the holes 32. The cutouts 44, 44' present flat sidewalls 44a, 44a' recessed inwardly from a cone defined by the threads 26. The sidewalls have holes 31 therethrough in communication with interior 30.

As best illustrated in FIGS. 2 and 3, the cutouts 44,44' are at angles β,β' for purposes that will become apparent. In a representative example, β is 65° and β' is 62°.

B. Distraction Spacer and Insertion Tool.

Figure 7:
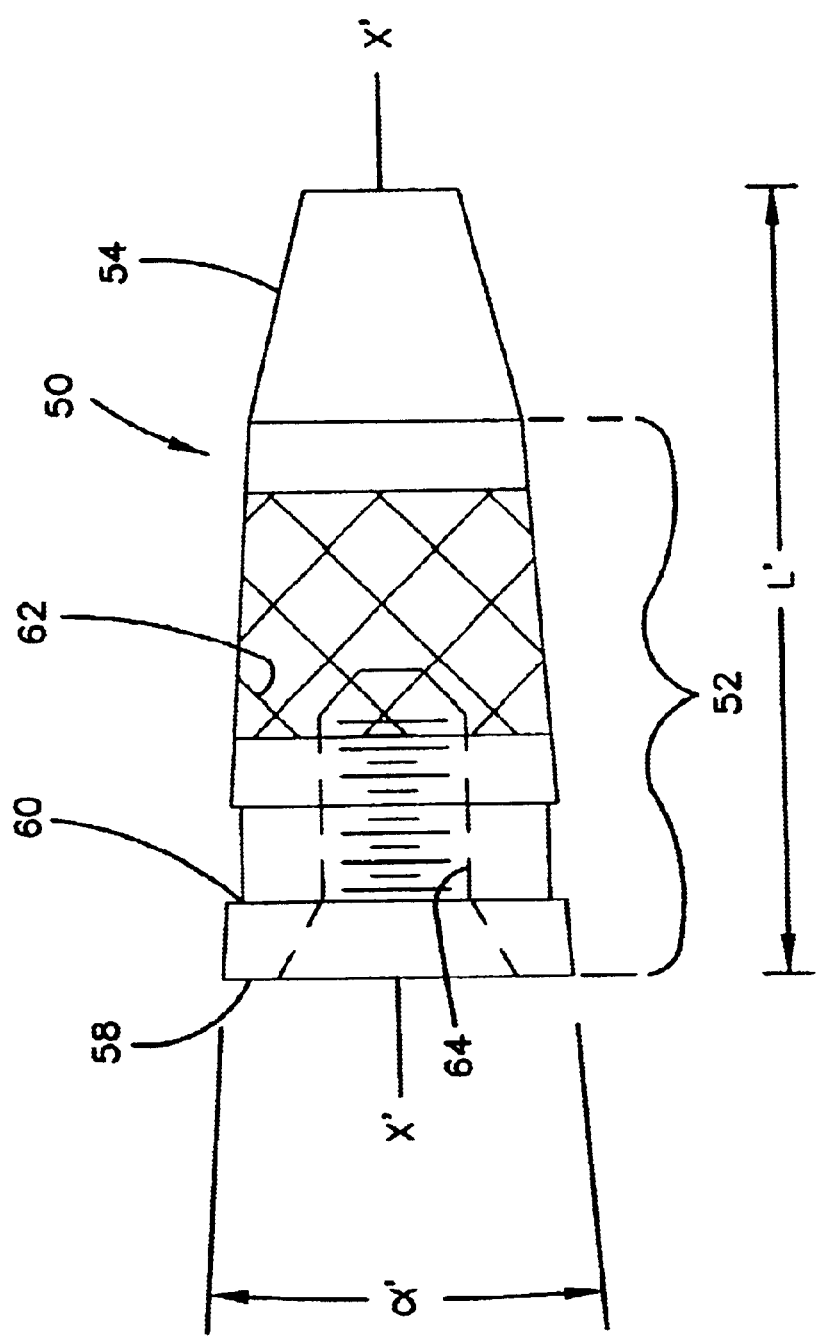
FIG. 7 is a side elevation view of a distraction plug for use in the present invention.

For use in placing the implant 20 between opposing vertebrae, a distraction spacer 50 is used. The distraction spacer 50 is shown in FIG. 7. The distraction spacer 50 is generally conical and has a main body portion 52 with a conical angle α' equal to the angle α of the implant 20. Accordingly, a kit containing numerous sized angles for an implant 20 may contain numerous sized distraction spacers with α' matching the implants 20.

Leading end 54 is provided with an additional taper to permit ease of insertion of the distraction spacer 50 into a disk space. Near the trailing end 58, the distraction spacer 50 includes an annular groove 60 to permit a surgeon to grasp the distraction spacer 50 if needed. The main body 52 is provided with a knurling 62 such that the distraction spacer 50 resists undesired movement following placement of the distraction spacer 50 into a disk space. The trailing end 58 is provided with an internally threaded axial bore 64 for attachment of a placement tool as will be described.

The distraction spacer 50 is sized to have an outer conical surface substantially equal to a conical surface defined by the minor diameters of the implant 20. Namely, at the trailing end 58, the diameter of the distraction spacer 50 is approximately equal to the trailing end minor diameter $D'_m$ of the implant 20. The distraction spacer is symmetrical about its longitudinal axis X'—X' and has an axial length L' approximate to the length L of the implant and sized for the distraction spacer 50 to be fully inserted into the disk space without protruding beyond the vertebrae.

Figure 7A:
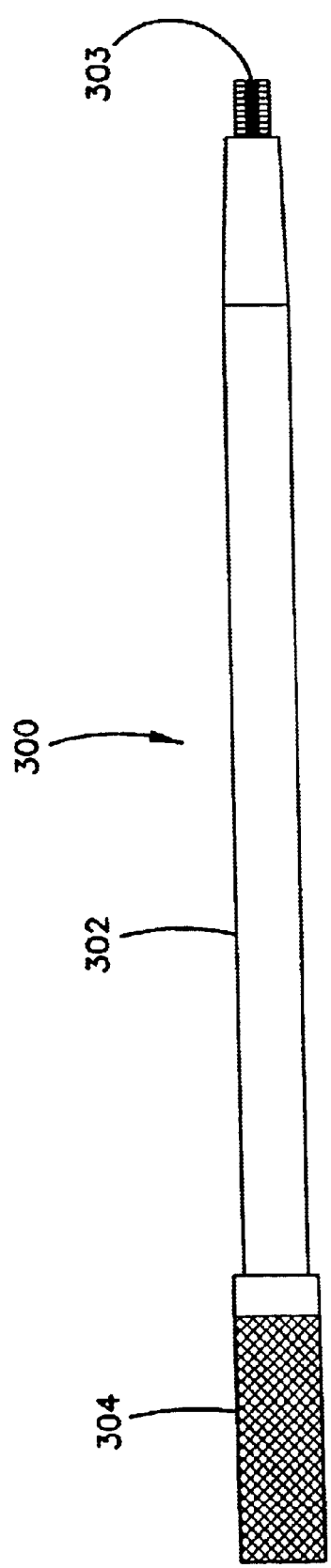
FIG. 7A is a side elevation view of a tool for placing the plug of FIG. 7.

FIG. 7A illustrates a tool 300 for placing plug 50. The tool 300 has a shaft 302 with a handle 304 at a proximal end. A threaded stud 303 is provided at the distal end. The stud 303 is threadedly received within bore 64 of plug 50 to axially align the longitudinal axes of the plug 50 and shaft 302.

C. Boring Tool.

FIG. 8 illustrates a pre-boring tool 70 for initial boring of the vertebrae prior to insertion of the implant and prior to tapping for the implant 20. The pre-boring tool 70 includes a shaft 71 having a tapered cutting head 72 (tapered at angle α) at a distal end of the tool 70.

A proximal end of the shaft 71 is provided with a stop flange 73 for limiting insertion of the boring tool 70 into a guiding drill tube (not shown). The shaft 71 includes enlarged diameter portions 74 to be in close tolerance with the internal diameter of a drill tube to ensure that the tool 70 does not have relative radial movement to a drill tube as the tool 70 is being axially advanced within a drill tube.

The cutting head 72 is provided with cutting teeth 75 to cut a tapered bore as the tool is rotated about its longitudinal axis X"—X". The teeth 75 are sized to cut a bore having a leading end diameter equal to the leading end minor diameter $D_m$ of the implant 20 and a trailing end diameter equal to the implant's trailing end minor diameter $D_M$. The distal end of the cutting head 72 is provided with an axially extended threaded bore 76 to receive a guide pin such as those shown as item 64 in FIG. 56 of the aforementioned U.S. Pat. No. 5,489,307 attached to pre-boring tool 112 in the '307 patent.

Such a guide pin is shown in. FIG. 10. The pin 200 has a tapered body 202 tapered at angle α with an axially extending stud 203 to be received within bore 76. A leading end 204 is provided with flutes 206 to remove disk material as the guide pin 200 is advanced. The selected guide pin 200 will have a diameter, $D_3$, equal to about 3 millimeters less than the diameter of a bore being cut by cutting head 72. A leading end diameter, $D_4$, is equal to the leading end diameter of the distraction spacer 50.

D. Tap.

FIGS. 11–13 illustrate a novel tap 80 for use in the method of the present invention. The tap 80 includes a shaft 81 having an axis X'''—X'''. A distal end of the shaft 81 is provided with a tapping head 82.

A proximal end of the shaft 81 is provided with stop flange 83 for limiting insertion of the tap 80 into a guiding drill tube (not shown). The shaft 81 includes enlarged diameter portions 84 sized to approximate an internal diameter of a guide tube (not shown) to ensure no relative radial movement of the tap 80 relative to a drill tube as the tap 80 is being axially advanced through a drill tube.

The novel tapping head 82 includes a hollow interior 86 with a closed axial or distal end 88. A thread pattern 90 surrounds the tapping head 82 but is spaced from the axial end 88 by an unthreaded guide tip 92.

Illustrated best in FIG. 13, the threads 90 are V-shaped in cross-section and extend from flat valleys 94 to pointed thread tips 96. The valleys 94 define a conical surface having an internal angle α" equal to the angle α of implant 20. Similarly, the tips 96 define a conical surface having an internal conical angle equal to α. The depth of the threads 96 (i.e., the distance between the tips 96 and the valleys 94) is equal to the depth of the threads 26 (i.e., the distance between the surfaces 26a and the valleys 28) of the implant 20.

The guide tip 92 is cylindrical and has a diameter $D_T$ equal to the leading end minor diameter $D_m$ of implant 20. The starting thread 90' accordingly has a minor diameter of the same size as the minor diameter $D_M$ of the starting thread of the implant 20. Also, starting thread 90' has a major diameter equal to the leading end major diameter $D_M$. The ending thread 90" has a minor diameter equal to the trailing end minor diameter $D'_m$ of implant 20. Further, the ending thread 90" has a major diameter equal to the major diameter $D'_M$ of the implant 20. The threading has a length $L_T$ equal to the length L of the implant 20. Accordingly, the thread pattern 90 is identical in sizing and angles to the thread pattern 26 of implant 20 except for the cross-section profile with threads 96 being V-shaped and with threads 26 being generally square in cross-section (best illustrated comparing FIGS. 6 and 13).

With reference to FIGS. 11 and 12, the thread pattern 96 includes three cutouts 100 to define cutting edges 102 to permit the threads 96 to tap a thread pattern as the cutting head is rotated in a counterclockwise direction in the view of FIG. 12. Channels 104 are provided from the cutouts 100 and extending into communication with the hollow interior 86. The channels 104 define pathways to permit debris formed by the tapping to be accumulated within the interior 86. Further, additional channels 106 are provided in the valleys 94 between opposing threads. The channels 106 further extend into communication with the interior 86 to provide additional pathways for debris to flow into the interior 86. Accordingly, during tapping with the tool 80, debris formed by the tapping is accumulated within the interior 86. Due to the closed end 88, the debris is retained within the interior 86 when the tap 80 is removed from the disk space.

E. Implant Driver.

FIGS. 14–17 illustrate a driver 110 for use in placing an implant 20 into a prepared space. The driver 110 includes a shaft 112. A distal end of the shaft 112 is provided with a driving head 114. A proximal end of the shaft 112 is provided with a handle 117.

The shaft 112 is hollow throughout its length defining an axially extending bore 113. The handle 117 includes a large diameter recess 115 and a narrower diameter recess 119. Recess 119 is threaded for reasons that will become apparent.

The driving head 114 includes axially extending gripping prongs 116,116'. The gripping prongs 116,116' are diametrically opposed and are positioned and shaped to be complementary to the cutouts 44,44', respectively of the implant 20. The side edges 116b' define an angle β* slightly less than angle β while the side edges 116b define an angle β*' slightly less than angle β'. For example, with reference to the dimensions given for β and β' in FIG. 2, the angle β* is about 63° and the angle β*' would be about 60° to permit minor relative rotational movement of the prongs 116,116' within the cutouts 44,44'.

As illustrated best in FIG. 17, the prongs 116,116' include threads 118 positioned and shaped to complete the thread pattern 26 of the implant 20. Namely, the implant 20 may be placed in the driving head 114 with the trailing end 24 abutting the end 112a of the shaft 112 and with the leading end 22 flush with the ends 116a, 116a' the prongs 116,116'. As a result, when the implant 20 is placed within the driving head 114, the prongs 116a, 116a' cover the sidewall openings 31 of the flat sidewalls 44a, 44a' of the implant 20 such that the implant 20 together with the prongs 116,116' define a continuous externally threaded frusto-conical shape and with the threads 26 aligned with the threads 118 to define a continuous thread pattern.

Figure 15A:
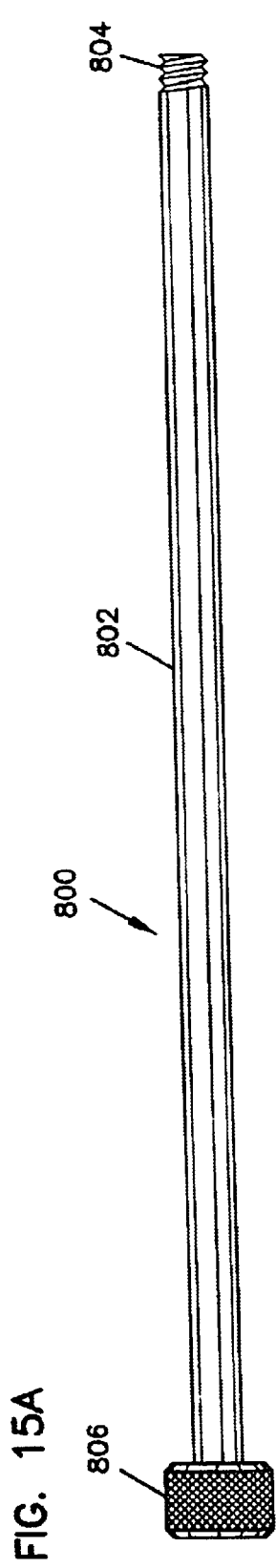
FIG. 15A is a side elevation view of a tool for holding the implant of FIG. 1 in the driver of FIG. 15.

In FIG. 15A, a tool 800 is shown to hold implant 20 in driver 110. The tool 800 has a shaft 802, a handle 806 and a threaded end 804. End 804 is threaded into the bore 40 of an implant 20 placed between prongs 116, 116'. When so positioned, the handle 806 is seated within recess 115 and shaft 802 extends through bore 113 to securely and releasably affix implant 20 within driver 110.

Figure 15B:
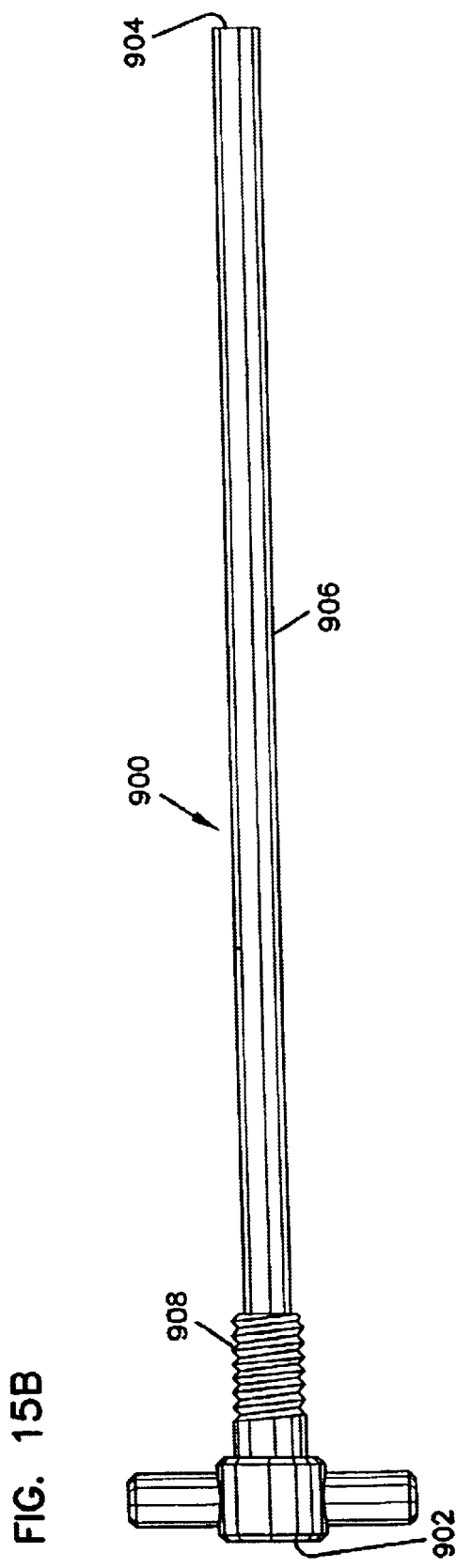
FIG. 15B is a side elevation view of a tool for releasing the implant of FIG. 1 from the driver of FIG. 15.

FIG. 15B shows a tool 900 for separating the implant 20 from the driver 110. With tool 800 removed from bore 113, the shaft 906 of tool 900 is placed in bore 113. The blunt end 904 abuts the trailing end 24 of the implant 20. A threaded portion 908 engages the threads of bore 119. By turning handle 902, the blunt end 904 urges the implant 20 out from between prongs 116, 116'.

F. Surgical Method.

Having thus described the novel implant 20, distraction spacer 50 and tools 70, 80, 110, the method of the present invention will now be described.

Figure 19:
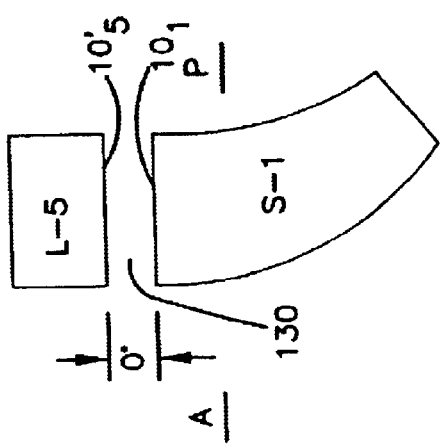
FIG. 19 is a side elevation schematic view of opposing L-5 and S-1 vertebrae prior to the method of the present invention.

With reference to FIG. 19, an L-5 and S-1 vertebrae are shown with a diseased disk space 130 between the opposing end plates $10'_5$ and $10_1$. For ease of illustration, disk material is not shown within the disk space 130. In the example of FIG. 19, the end plates $10'_5$ and $10_1$ are in parallel alignment and are to be distracted (i.e., separated) as well as being provided with a desired lordosis which in the example is 8°.

As illustrated in FIG. 24 (which is a view from the anterior to the posterior), a sagittal plane S divides the vertebrae into a left side L and a right side R. A preferred surgical approach is an anterior approach performed laparoscopically. Procedures such as removal of disk material are not described or illustrated and are known in the art.

A selected distraction spacer 50 (i.e., a distraction spacer sized and provided with a conical angle selected by the physician to attain a desired distraction and lordosis) is attached to tool 300 with the shaft threaded into the threaded bore 64. The distraction spacer 50 is forced into space 130 on the left side until the distraction spacer 50 is fully received within the disk space such that the end 58 does not protrude out of the disk space. The tool 300 is then unthreaded from the distraction spacer 50 and removed through the drill tube leaving the distraction spacer in place.

Figure 20:
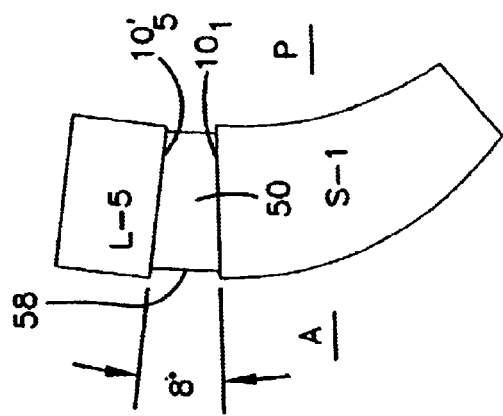
FIG. 20 is the view of FIG. 19 following placement of the distraction plug of FIG. 7.

With the examples given, the distraction spacer 50 urges the disks L-5 and S-1 apart by reason of the conical surface of the distraction spacer urging against the end plates $10'_5$ and $10_1$. In addition to distracting the vertebrae L-5 and S-1, the distraction plug 50 induces a desired lordosis of 8° to the vertebrae L-5 and S-1 as illustrated in FIG. 20.

Leaving the distraction spacer 50 in place, a drill tube (not shown but which may be such as that shown in U.S. Pat. No. 5,489,307) is placed on the right side of the disk space 130. A bore is then formed partially into the opposing vertebrae L-5 and S-1 as illustrated in FIG. 21. To form the bore, the pre-boring tool 70 with an attached guide pin 200 is first inserted into drill tube. The guide point acts against the opposing surfaces of the end plates $10_5'$, 10, to initially centrally align the boring tool 70 within the disk space 130.

By rotating the pre-boring tool 70, the cutting head 72 cuts an initial depth of a bore into the vertebrae L-5, S-1. Due to guide 200, a bore is cut by head 72 only about 50% of the way into the disk space.

It will be appreciated that pre-boring tools such as tool 70 having guide pins to initially form a bore between opposing vertebrae is not part of this invention per se and is disclosed and described in U.S. Pat. No. 5,489,307. The '307 patent further discloses forming a final bore with a final boring tool. Since the vertebrae L-5 and S-1 are distracted with a lordosis of 8° and the boring tools having cutting heads which are tapered, a bore is only partially cut into the vertebrae by the pre-boring tool with no bore formation at the posterior ends of the vertebrae L-5, S-1. The posterior end will be simultaneously bored and tapped by the debris retaining tap.

After the formation of the desired bore by the boring tool 70, the tap 80 is inserted into the drill tube as illustrated in FIG. 22. The minor diameter of the threads of the tap 80 will be substantially equal to the spacing of the end plates such that the V-shaped threads 90 of the tap only cut into the end plates 10₅', 10, as illustrated in FIG. 22.

Since the tap 80 is provided with a conical angle substantially equal to the angled separation of the distracted vertebrae, the tap 80 forms a tapped bore between the vertebrae L-5, S-1 with a thread pattern matching the thread pattern of the implant 20. After removal of the tap, debris formed in the tapping process is removed from the disk space 130 by reason of the debris being captured within the interior 86 of the tapping head 82.

With the tapping operation complete, the implant 20 is inserted into the distal end of the driver 110 and retained therein by tool 802. The implant 20 is filled with bone or other suitable bone growth inducing substance. The driver 110 and attached implant 20 are then inserted through the drill tube and threadedly urged into the pre-tapped bore between the vertebrae L-5 and S-1.

As mentioned, the pre-tapped bore matches the size and thread pattern of the implant 20 except only that the pre-tapped threads of the bore are V-shaped and the threads 26 of the implant 20 are square in cross-section. By reason of this difference in geometry of the threads, forcing the square cross-section threads 26 of the implant into the V-shaped tapped threads causes material of the vertebrae to be compressed as the implant is inserted into the disk space 130. This compression further increases distraction and securely lodges the implant 20 within the disk space 130 to prevent undesired movement of the implant 20 relative to the vertebrae.

Rotation of the implant and driver within the disk space is continued until the implant 20 is fully inserted within the disk space 130 and the prongs 116,116a' are aligned with the disk space 130. With the prongs 116, 116a' so aligned, the holes 32 directly oppose the bone of the vertebrae L-5, S-1. The implant 20 and boring and tapping tools 110, 80 are sized such that the tapping exposes the cancellous bone of the vertebrae to encourage bone growth from the vertebrae through the implant and in communication with any bone growth inducing substance placed within the interior 30 of the implant. Also, the threads 26 of the implant 20 will be opposing and retained within the cortical bone of the vertebrae L-5, S-1 to resist subsidence of the implant 20 into the vertebrae.

With the implant finally positioned, the driving tool 110 is removed by axially pulling on the tool. Due to frictional forces, the driving tool 110 may resist removal. In such an event, the removal tool 900 may be inserted within the bore 113 forcing separation of the tool 110 from the implant 20 to facilitate ease of removal.

FIG. 24 illustrates an implant 20 inserted between the vertebrae L-5, S-1 on the right side and with a distraction spacer 50 still in place on the left side. After insertion of an implant 20 on a right side, the guide tube may be moved to the left side. The distraction spacer 50 may then be removed and the left side may be prepared for implant insertion by boring and tapping as described above and a second implant may be placed in the left side.

V. DESCRIPTION OF ALTERNATIVE IMPLANT AND DISTRACTION SPACER EMBODIMENTS

A. Implant

Referring to FIGS. 25–30, another embodiment of an implant is shown. The implant 400 can be used with the tools and methods described above. According to this embodiment, the implant 400 has a first and second taper and a longitudinal axis X—X extending from a leading end 401 to a trailing end 402. The trailing end 402 of the present embodiment comprises a "trailing end rise" (TER) 403 and a terminal end 404. The first taper of implant 400 diverges from the axis from the leading end 401 to the trailing end rise 403 of the trailing end 402. The second taper diverges from the axis from the terminal end 404 to the TER 403. The trailing end rise is the region of greatest diameter of the implant 400. As described below, the second taper provides implantation advantages for the surgeon as well as increased safety for the patient.

The bi-tapered implant 400 includes leading end 401 having a first taper providing a substantially frusto-conical shape with a conical angle α equal to a desired lordosis between selected vertebrae. The angle α of the illustrated embodiment, measured from the leading end 401 to the TER 403 is 8°, however, as described for other embodiments of the invention, the implants will be available with a variety of angles and sizes.

Figure 25:
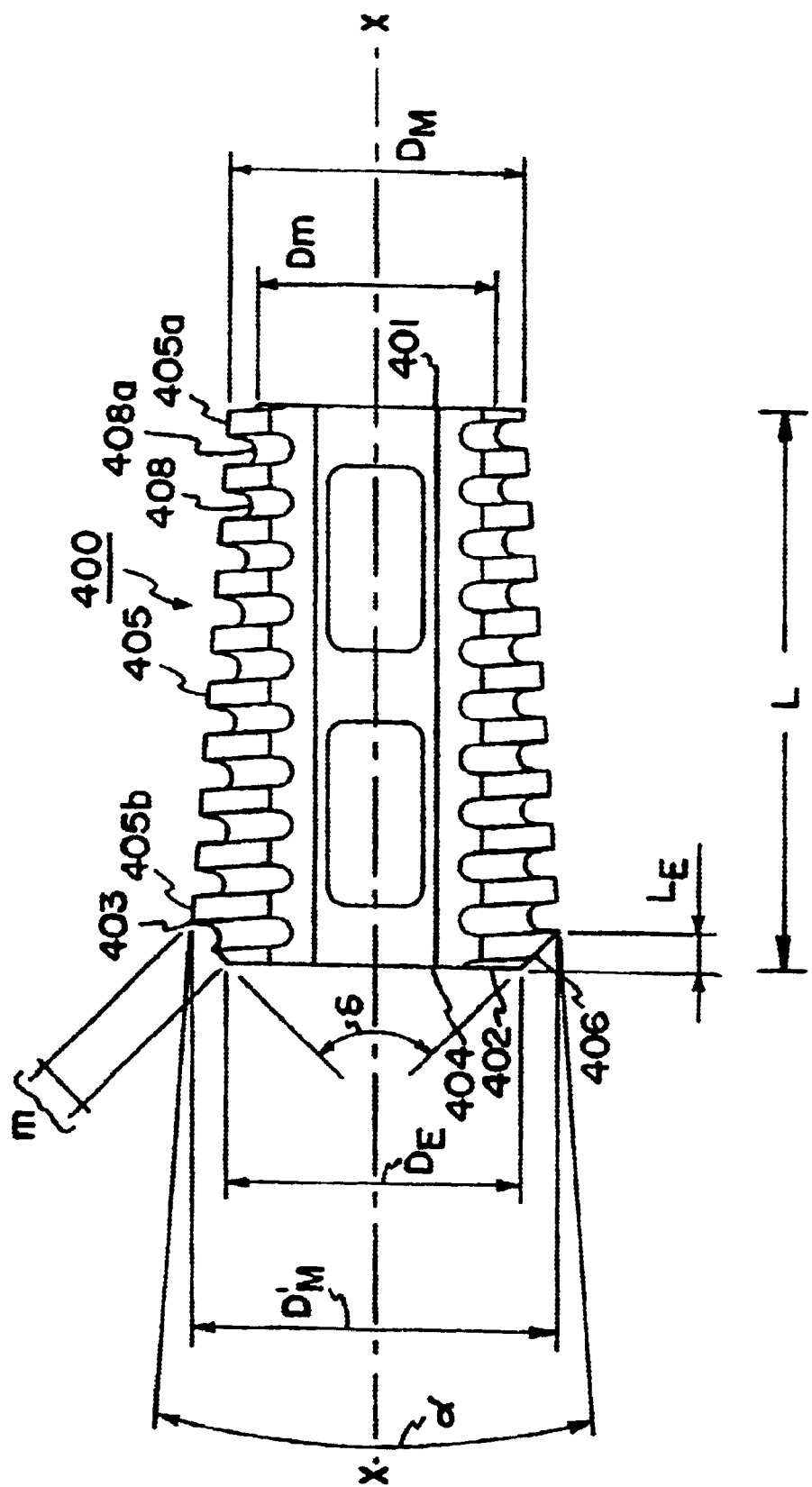
FIG. 25 is a right side elevation view of an, embodiment for a lordotic implant according to the present invention illustrating a first and second taper (the opposite side being identical in appearance)

Referring to FIG. 25, leading end 401 has a major diameter $D_M$ measured between diametrically opposite outer radial surfaces 405a of the threads 405 at the leading end 401. The leading end 401 also has a minor diameter $D_m$ measured between diametrically opposite inner radial surfaces 408a of the valleys 408 of the thread pattern 405 of implant 400.

At the trailing end 402, the implant 400 has a major diameter $D'_M$ measured between diametrically opposite outer radial surfaces 405b of threads 405 at the trailing end rise 403. The trailing end 402 also has a minor diameter $D_E$ measured across terminal end 404.

The second taper of implant 400 has a second angle, δ, extending from the terminal end 404 to the TER 403. The angle δ will vary with the diameter $D'_M$ of the TER 403, the diameter $D_E$ of the terminal end 404, and the longitudinal distance $L_E$ therebetween. In the illustrated embodiment, the diameter $D_E$ of the terminal end 404 is equal to the major diameter $D_M$ of the leading end 401.

The longitudinal distance $L_E$ can be about 5% to 25% of the overall length L of the implant. Generally, $L_E$ is less than 15% of the overall length L, typically about 8–10%.

It will be appreciated that the slope "m" of the second taper, relative to the longitudinal axis X—X, can be calculated by the equation:

$$D'_M - D_E / L_E$$

In the illustrated embodiment, m is about 1 (45°). However, the actual slope dimension m can vary, typically, between 0.58 (30°) and 1.73 (60°).

Figure 28:
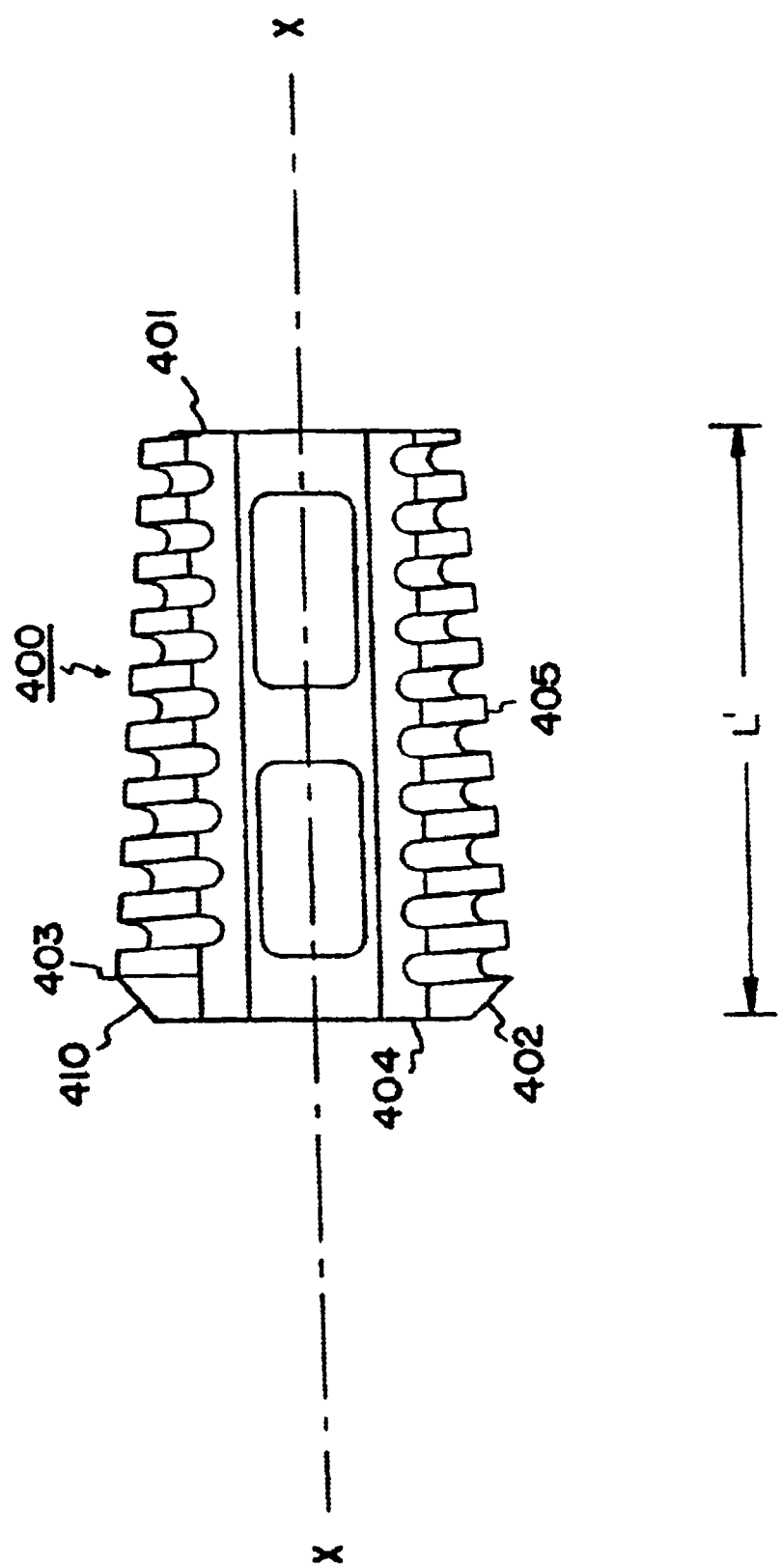
FIG. 28 is a right side elevation view of an alternative embodiment of a lordotic implant according to the present invention illustrating a first and second taper (the opposite side being identical)
Figure 30:
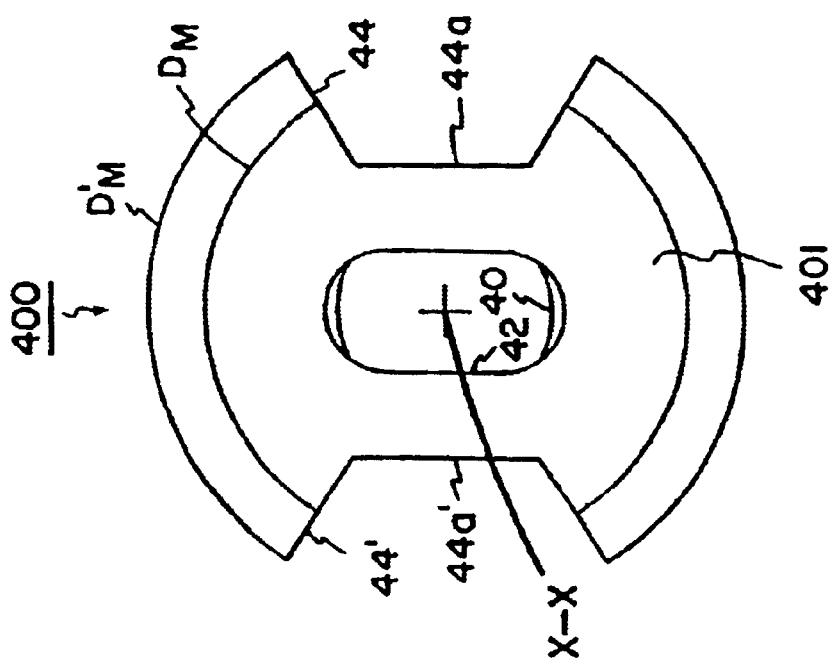
FIG. 30 is an elevation view of a leading end of the implant of FIG. 25.
Figure 29:
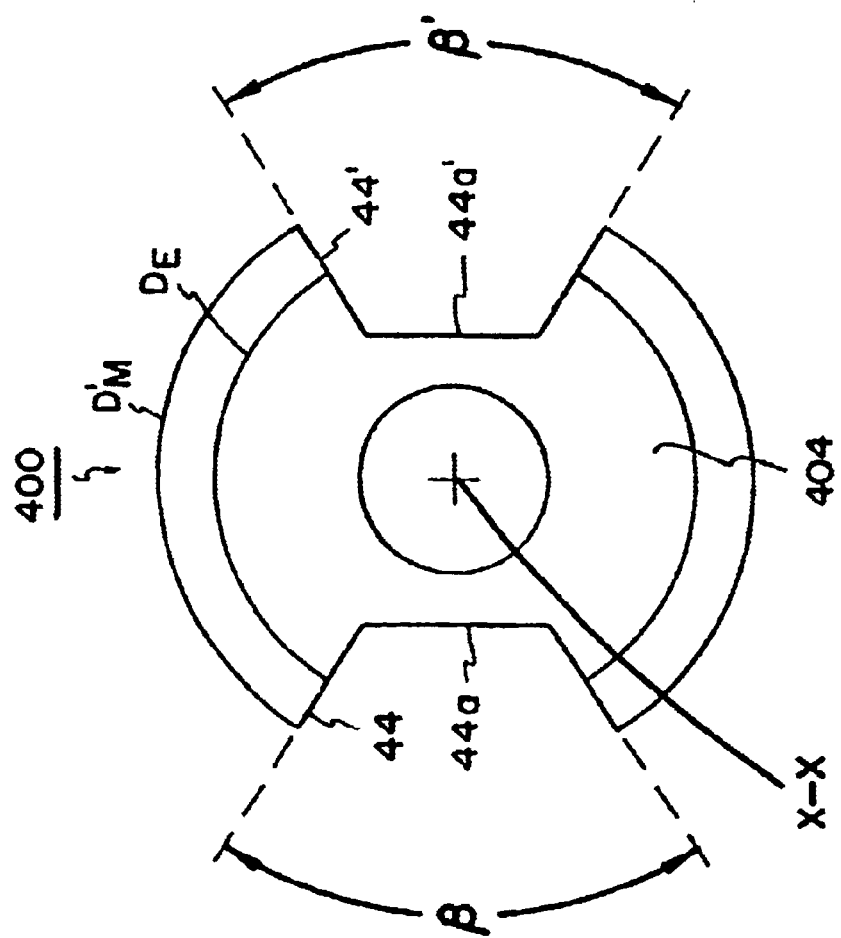
FIG. 29 is an elevation view of a terminal end of the implant of FIG. 25.

The helical threads 405 can extend along the second taper as illustrated at 406 of FIGS. 25–27. Alternatively, as illustrated in FIG. 28, the threads 405 can stop at the terminal rise 403 and the second taper comprise a flat 410, undulating or other non-thread bearing surface, from trailing end rise 403 to terminal end 404. FIGS. 29 and 30 illustrate the terminal end and leading end, respectively, of implant 400. Other features described for the implant embodiment 20 are also applicable to implant 400.

The second taper of implant 400 provides installation advantages for the surgeon and enhanced safety features for the patient. For the surgeon, the trailing end taper allows a greater margin of error in the desired length of the bore formed for inserting the implant. That is, in some circumstances, if the length of the bore formed is less than the length of the implant, the tapered trailing end 402 permits insertion of implant 400 into the "short" bore without leaving a trailing end exposed beyond the surface of the vertebrae that has a sharp or abrupt edge. In addition, once implanted during surgery, the tapered trailing end of implant 400 facilitates re-engaging the implant driver to adjust the anterior/posterior position of the implant.

For patient safety, once placed between the end plates of opposing vertebrae, should the implant 400 back out or become displaced, the second taper at the trailing end reduces the likelihood that the trailing end would erode through major blood vessels, the peritoneum or other structures surrounding the implanted device.

B. Distraction Spacer

Figure 31:
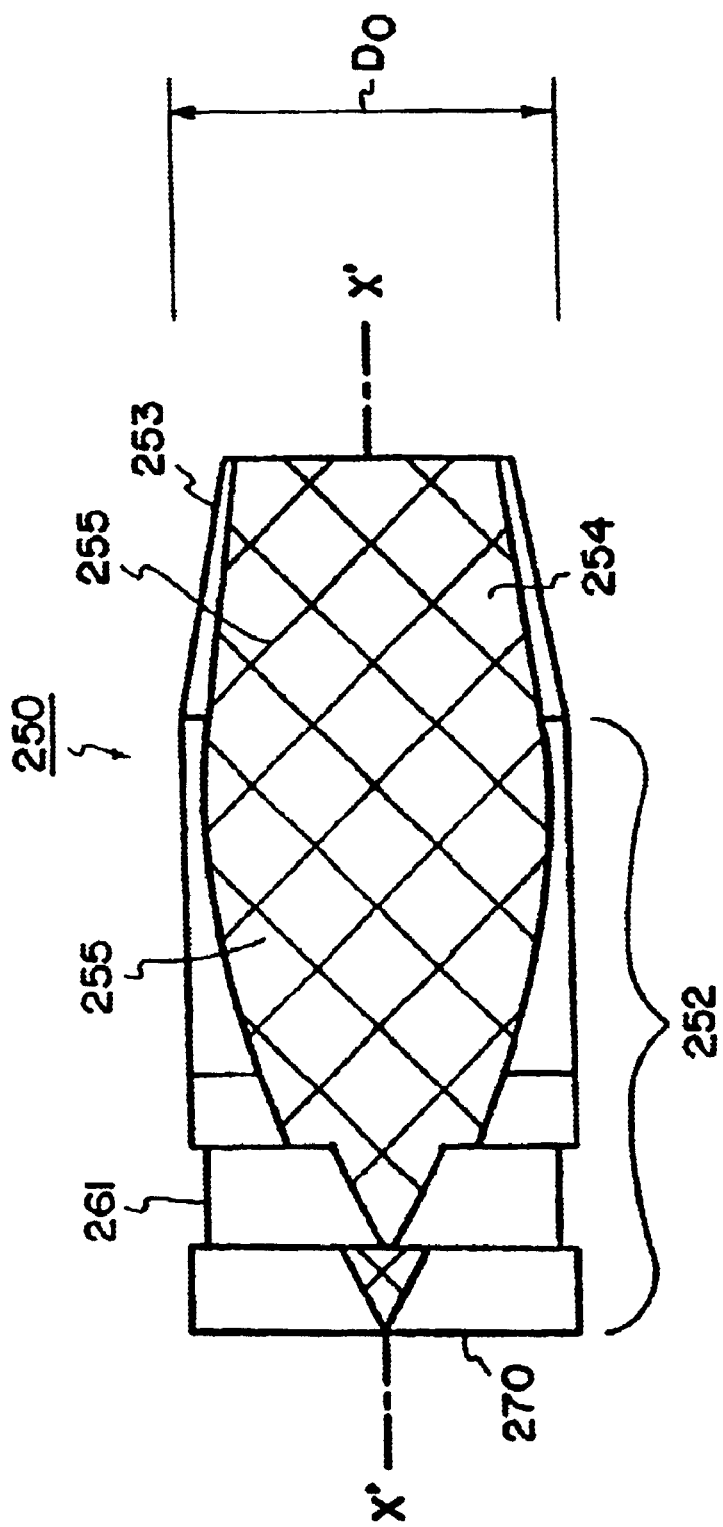
FIG. 31 is a side elevation of an embodiment of a distraction plug of the invention (the opposite side being identical in appearance)

FIGS. 31–36 illustrate additional embodiments of a distraction spacer ("plug") suitable for use with lordotic implants or non-tapered type implants. FIG. 31 is a side elevation view of a ramp distraction spacer 250, the opposite side being identical in appearance. The spacer 250 has a main body portion 252 with a leading end 253. The ramp surface 254 of spacer 250 is shown in FIG. 31. In transverse cross section, the region of the main body 252 and leading end 253 between the ramp surfaces 254 can be arcuate. It will be appreciated that ramp surface(s) 254 includes knurls 255 to reduce the chance of undesired movement following placement of distraction spacer 250 into a disk space.

Figure 32:
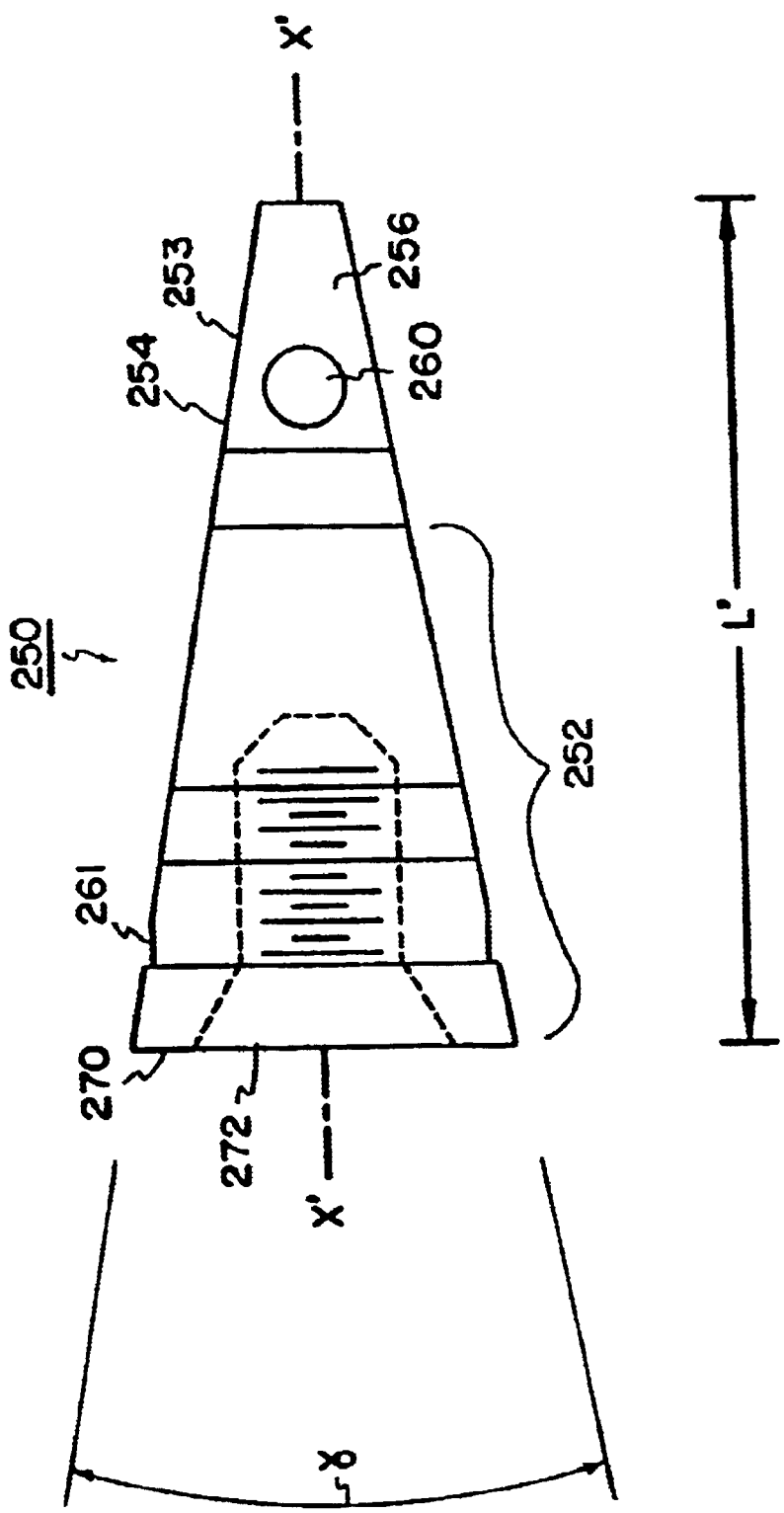
FIG. 32 is a side elevation of the distraction plug of FIG. 31 rotated 90° from the view of FIG. 31 (the opposite side being identical in appearance)
Figure 33:
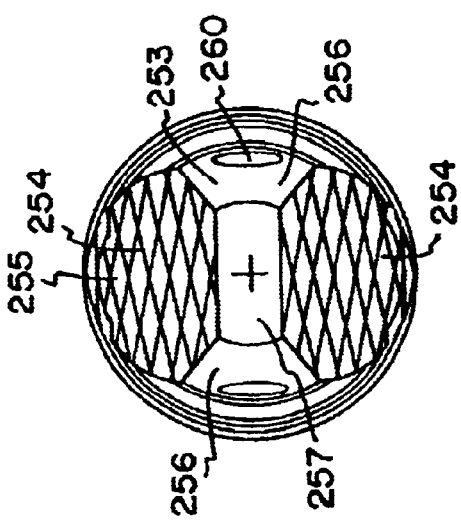
FIG. 33 is a frontal view of the leading end of the distraction plug of FIGS. 31 and 32.

FIG. 32 is a right side elevation of the distraction spacer 250 rotated 90° around longitudinal axis X'—X' from the view in FIG. 31. The opposite side of the view of FIG. 32 is identical in appearance. A front view of the tapered surface 256 of the leading end 253 is shown in FIG. 32. The relationship of the ramp surfaces 254 and the tapered surfaces 256 at the leading end 253 is illustrated in FIG. 33. It will be appreciated that the leading end tip 257 need not be circular but can, for example, be oval in shape.

The ramp surfaces 254 of the distraction spacer 250 are symmetrically opposed about the longitudinal axis X'—X' and form a ramp angle of γ. The angle γ and leading end tip 257 size are selected to permit ease of insertion of the distraction spacer 250 into the disk space. The distraction spacer is sized to have a main body 252 outer diameter $D_o$ substantially equal to the midline disk height of a healthy disk in the patient being treated. The axial length L' of the distraction spacer 250 is approximate to the length L of the implant and sized for the distraction spacer 250 to be fully inserted into the disk space without protruding beyond the vertebrae.

Leading end 253 can also include a bore 260 which passes through opposing tapered surfaces 256. The bore 260 provides for insertion of pin 351 of T-device 350 illustrated in FIG. 37. T-device 350 can facilitate removal of the spacer 250 from, for example, tool 300 illustrated in FIG. 7A. The T-device 350 also includes a handle 352 for grasping the device.

Near the trailing end 270, the distraction spacer 250 includes an annular groove 261 to permit a surgeon to grasp the distraction spacer if needed. The trailing end 270 is provided with an internally threaded axial bore 272 for attachment of a placement tool 300.

Figure 34:
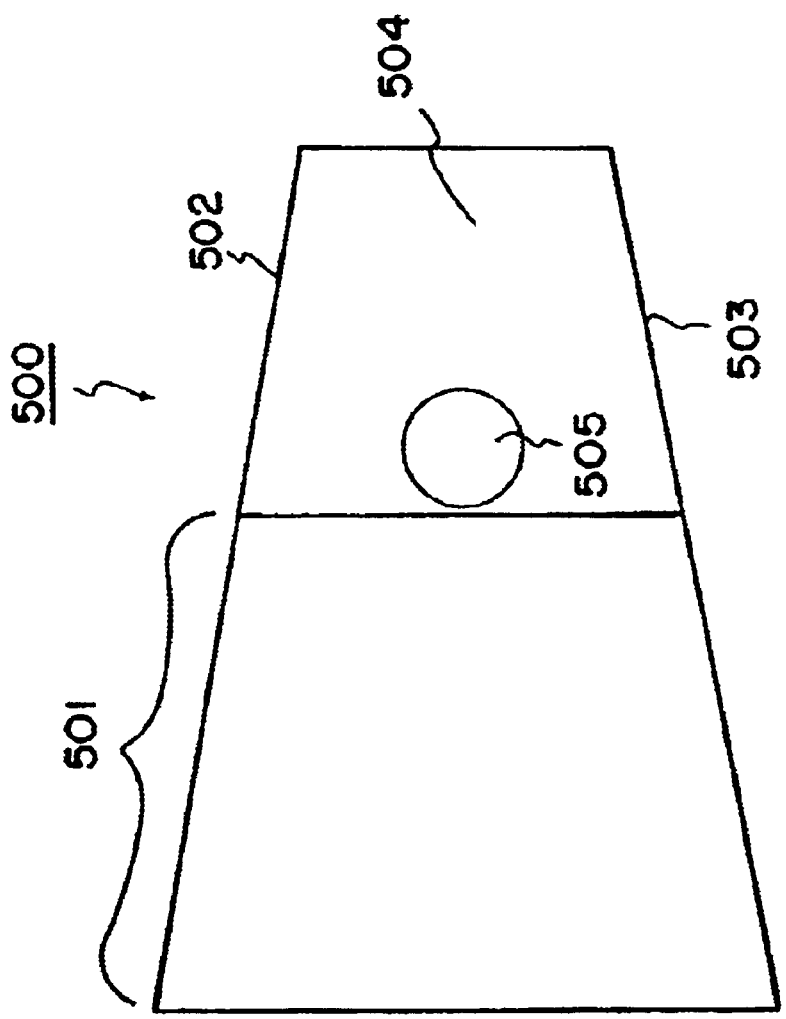
FIG. 34 is a side elevation of an alternative embodiment of a distraction plug of the invention (the opposite side being identical in appearance)
Figure 35:
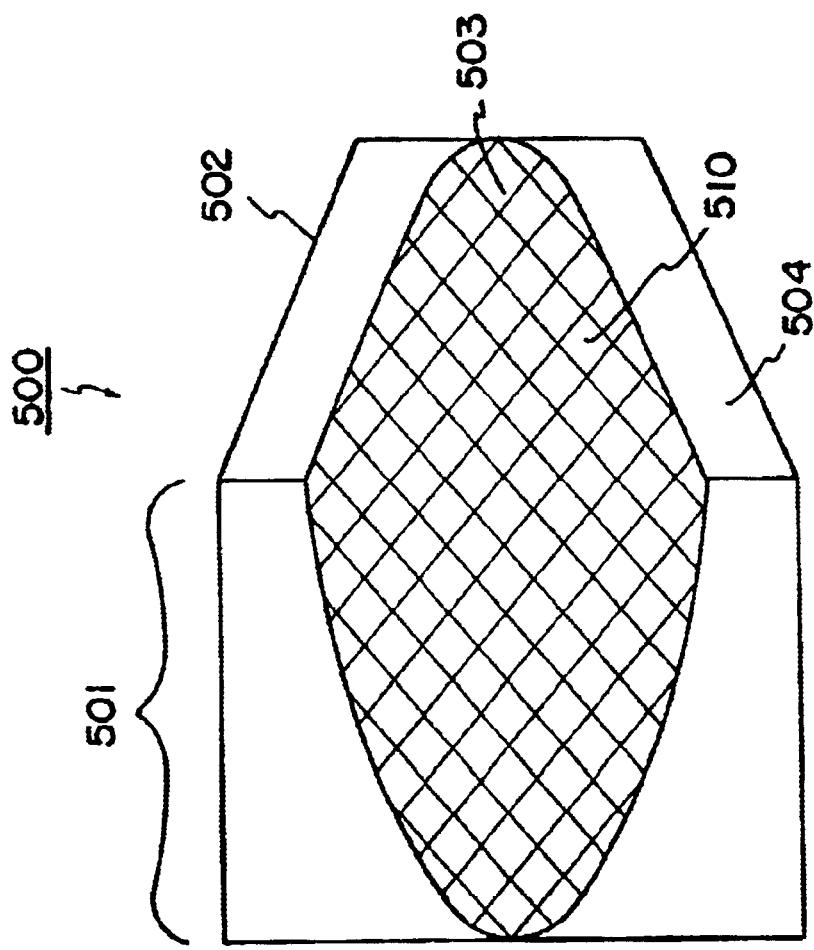
FIG. 35 is a side elevation of the distraction plug of FIG. 34 rotated 90° from the view of FIG. 34 (the opposite side being identical in appearance)

FIG. 34 is a side elevation view of another embodiment of a ramp distraction spacer 500, the opposite side being identical in appearance. The spacer 500 has a main body portion 501 with a leading end 502. FIG. 35 is a side elevation view of the distraction spacer 500 rotated 90° around longitudinal axis X'—X' from the view in FIG. 34, the opposite side of the view being identical in appearance. FIG. 35 illustrates the ramp surface 503 of spacer 500 including knurls 510. It will be appreciated that the embodiment of distraction spacer 500 does not include the annular groove 261 present in distraction spacer 250 (see FIGS. 31–33).

Figure 36:
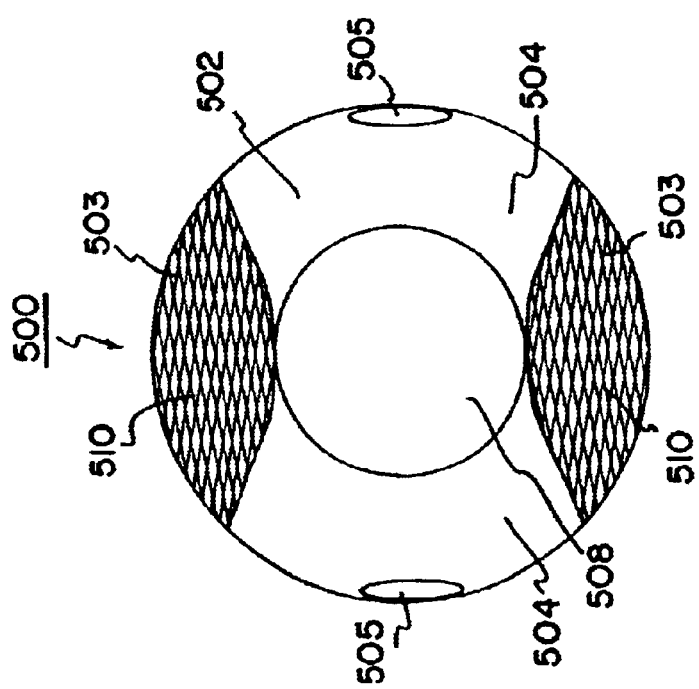
FIG. 36 is a frontal view of the leading end of the distraction plug of FIGS. 34 and 35.

The relationship of the tapered surface 504 of leading end 502 and ramp surfaces 503 are illustrated in the front end view of FIG. 36. A bore 505 may also be present for operation of T-device 350. The leading end tip 508 of the illustrated embodiment of implant 500 is circular.

As discussed above, a kit containing numerous sized implants can be provided with numerous sized distraction spacers having various ramp angles.

With the invention as described, implants may maintain or increase lordosis. Further, the present invention permits formation of a tapped hole while removing debris which would otherwise obstruct implant insertion. With the present invention, precise identity of depth of insertion of an implant on the left and the right side need not be attained, permitting greater versatility and tolerance of the method of the present invention to inaccuracies.

Having disclosed the invention in a preferred embodiment, modifications and equivalents of the disclosed concepts may occur to one skilled in the art. It is intended that the scope of the present invention not be limited to the specific embodiments disclosed, but shall include such modifications and equivalents.

What is claimed is:

1. A kit for preparing a disk space between opposing vertebrae, said kit comprising:
    a distraction spacer for distracting the opposing vertebrae, the distraction spacer having:
        a main body;
        first and second diametrically opposed surfaces having a leading end and a trailing end with a longitudinal axis passing therethrough;
        said first and second diametrically opposed surfaces converging towards said longitudinal axis from said trailing end to said leading end; and
    a tap sized to tap the opposing vertebrae distracted by the distraction spacer having:
        a shaft defining a longitudinal axis;
        a head at a distal end of said shaft;
        a tapping thread at least partially surrounding said head, said tapping thread including a plurality of peaks and valleys around said head, said thread being provided between a leading end and a trailing end of said head, the thread defining an outer diameter that decreases in size in a direction extending from the trailing end to the leading end of said head, said diameter at the leading end of said head being substantially equal to an implant leading end diameter.

2. The kit according to claim 1 wherein said main body is frusto-conical shaped and said first and second diametrically opposed surfaces are portions of said frusto-conical shape.

3. The kit according to claim 1 wherein said first and second diametrically opposed surfaces are flat surfaces.

4. The kit according to claim 3 wherein said main body between said diametrically opposed surfaces is arcuate.

5. The kit according to claim 4 wherein said distraction spacer further comprises a bore passing through said main body arcuate surfaces.

6. The kit according to claim 1 wherein said distraction spacer further comprises an internal axial threaded bore at said trailing end.

7. The kit according to claim 1 wherein said leading end further comprises a bore passing through said first and second diametrically opposed surfaces.

8. The kit according to claim 1 wherein said diametrically opposed surfaces define an angle substantially equal to a desired degree of lordosis.

9. The kit according to claim 1 wherein said diametrically opposed surfaces are disposed on a substantially continuous outer surface of said main body symmetrically about said longitudinal axis of said main body.

10. The kit according to claim 1 wherein said diametrically opposed surfaces comprise knurls.

11. The kit according to claim 1 wherein said distraction spacer further comprises an annular groove near said trailing end.

12. The kit according to claim 1 wherein said tapping head includes a hollow body defining a tap interior and a plurality of channels for directing tapped debris from said tapping thread into said tap interior.

13. The kit according to claim 12 wherein said tapping thread includes a plurality of axially extending grooves through said thread, said channels formed through said grooves and into said interior.

14. The kit according to claim 12 wherein said channels are formed through said valleys.

15. The kit according to claim 12 wherein said interior is closed at said distal end of said head.

16. The kit according to claim 1 wherein said tapping thread has a sharp radial extremity.

17. The kit according to claim 1 wherein the head defines a length between the leading end and the trailing end, and wherein the outer diameter tapers along substantially the entire length.

18. A kit for preparing a disk space between opposing vertebrae, said kit comprising:
    a distraction spacer for distracting the opposing vertebrae, the distraction spacer having:
        a main body having first and second opposed surfaces and first and second ends with a longitudinal axis passing therethrough;
        a first diameter at a point near the first end and a second diameter at a point near the second end;
        said first diameter being smaller than said second diameter; and
    a tap sized to tap the opposing vertebrae distracted by the distraction spacer having:
        a shaft defining a longitudinal axis;
        a head at a distal end of said shaft, said head having first and second ends;
        a tapping thread at least partially surrounding said head, said thread being provided between the first end and the second end of said head, the thread defining an outer diameter that decreases in size in a direction extending from the second end to the first end of said head, said first end and second end having diameters substantially equal to first and second end diameters of an implant.

19. The kit according to claim 14 wherein said main body is frusto-conical shaped and said first and second opposed surfaces are portions of said frusto-conical shape.

20. The kit according to claim 14 wherein said first and second opposed surfaces are flat surfaces.

21. The kit according to claim 18 wherein said main body between said opposed surfaces is arcuate.

22. The kit according to claim 18 wherein said distraction spacer further comprises an internal axial threaded bore at said second end.

23. The kit according to claim 18 wherein said opposed surfaces define an angle substantially equal to a desired degree of lordosis.

24. The kit according to claim 18 wherein said opposed surfaces comprise knurls.

25. The kit according to claim 18 wherein said head includes a hollow body defining a tap interior and a plurality of channels for directing tapped debris from said tapping thread into said tap interior.

26. The kit according to claim 25 wherein said tapping thread includes a plurality of axially extending grooves through said thread, said channels formed through said grooves and into said interior.

27. The kit according to claim 25 wherein an axial end of said interior is closed at said distal end.

28. The kit according to claim 18 wherein said tapping thread has a sharp radial extremity.

29. The kit according to claim 18 wherein said tapping thread has a diameter that increases in size from said first end of said tap head to said second end of said tap head.

30. The kit according to claim 18 wherein the head defines a length between the first end and the second end, and wherein the outer diameter tapers along substantially the entire length.

31. A kit for placing an implant into a disk space between opposing vertebrae, the implant including a implant body having a first end and a second end, the implant body having an implant thread pattern surrounding the implant body, the implant body also including a major diameter and a minor diameter adjacent the first end, the implant body further including a major diameter and a minor diameter adjacent the second end, the kit comprising:
    a distraction spacer for distracting opposing vertebrae prior to placement of the implant, the spacer having:
        a distraction body having first and second ends, the distraction body defining a first diameter at a location near the first end of the distraction body, the first diameter of the distraction body being generally equal to the minor diameter at the first end of the implant body, the distraction body also defining a second diameter at a location near the second end of the distraction body, the second diameter of the distraction body being generally equal to the minor diameter at the second end of the implant body, the distraction body further including a lordotic taper extending between the first diameter and the second diameter; and
    a tap sized to tap the opposing vertebrae distracted by the distraction spacer, the tap including:
        a threaded tap body that defines a first minor diameter at one location on the tap body, the first minor diameter of the tap body being generally equal to the minor diameter at the first end of the implant body, the tap body also defining a second minor diameter at a second location on the tap body, the second minor diameter of the tap body being generally equal to the minor diameter at the second end of the implant body, and the tap body defining a lordotic taper that extends between the two locations on the tap body.

32. A kit for placing an implant into a disk space between opposing vertebrae according to claim 31, wherein the tap body defines a first major diameter at a first location on the tap body, the first major diameter of the tap body being generally equal to the major diameter at the first end of the implant body, and wherein the tap body defines a second a major diameter at a second location on the tap body, the second major diameter of the tap body being generally equal to the major diameter at the second end of the implant body.

33. A kit for preparing a disk space between opposing vertebrae, said kit comprising:
    a distraction spacer having:
        a main body;
        first and second diametrically opposed surfaces having a leading end and a trailing end with a longitudinal axis passing therethrough;

said first and second diametrically opposed surfaces converging towards said longitudinal axis from said trailing end to said leading end and said first and second diametrically opposed surfaces are flat surfaces, wherein said main body between said diametrically opposed surfaces is arcuate; and a tap having:
   a shaft defining a longitudinal axis;
   a head at a distal end of said shaft;
   a tapping thread at least partially surrounding said head, said tapping thread including a plurality of peaks and valleys around said head with a leading end tap diameter adjacent a distal end of said head and with a trailing end tap diameter spaced from said distal end of said head, said trailing end tap diameter being greater than said leading end tap diameter, said leading end tap diameter being substantially equal to an implant leading end diameter.

34. A kit according to claim 33, wherein said distraction spacer further comprises a bore passing through said main body arcuate surfaces.

35. A kit for preparing a disk space between opposing vertebrae, said kit comprising:
   a distraction spacer having:
      a main body;
      first and second diametrically opposed surfaces having a leading end and a trailing end with a longitudinal axis passing therethrough;
      said first and second diametrically opposed surfaces converging towards said longitudinal axis from said trailing end to said leading end, said diametrically opposed surfaces comprising knurls; and
   a tap having:
      a shaft defining a longitudinal axis;
      a head at a distal end of said shaft;
      a tapping thread at least partially surrounding said head, said tapping thread including a plurality of peaks and valleys around said head with a leading end tap diameter adjacent a distal end of said head and with a trailing end tap diameter spaced from said distal end of said head, said trailing end tap diameter being greater than said leading end tap diameter, said leading end tap diameter being substantially equal to an implant leading end diameter.

36. A kit for preparing a disk space between opposing vertebrae, said kit comprising:
   a distraction spacer having:
      a main body having first and second opposed surfaces and first and second ends with a longitudinal axis passing therethrough, wherein said main body between said opposed surfaces is arcuate;
      a first diameter at a point near the first end and a second diameter at a point near the second end;
      said first diameter being smaller than said second diameter; and
   a tap having:
      a shaft defining a longitudinal axis;
      a head at a distal end of said shaft, said head having first and second ends, a first diameter near the first end and a second diameter near the second end, wherein said first diameter is smaller than said second diameter, and said first and second diameters being substantially equal to first and second diameters of an implant;
      a tapping thread at least partially surrounding said head.

37. A kit for preparing a disk space between opposing vertebrae, said kit comprising:
   a distraction spacer having:
      a main body having first and second opposed surfaces and first and second ends with a longitudinal axis passing therethrough, wherein said opposed surfaces comprise knurls;
      a first diameter at a point near the first end and a second diameter at a point near the second end;
      said first diameter being smaller than said second diameter; and
   a tap having:
      a shaft defining a longitudinal axis;
      a head at a distal end of said shaft, said head having first and second ends, a first diameter near the first end and a second diameter near the second end, wherein said first diameter is smaller than said second diameter, and said first and second diameters being substantially equal to first and second diameters of an implant;
      a tapping thread at least partially surrounding said head.

38. A tap for tapping opposing vertebrae prior to placement of an implant, the implant having first and second ends and defining a lordotic taper that extends from the first end to the second end, the tap comprising:
   a threaded tap body defining a lordotic taper that generally matches the lordotic taper that extends from the first end to the second end of the implant.

* * * * *